US005946371A

United States Patent [19]
Lai

[11] Patent Number: 5,946,371
[45] Date of Patent: Aug. 31, 1999

[54] METHOD AND APPARATUS FOR VOLUMETRIC COMPUTED TOMOGRAPHY SCANNING WITH OFFSET SYMMETRIC OR ASYMMETRIC DETECTOR SYSTEM

[75] Inventor: Ching-Ming Lai, Wakefield, Mass.

[73] Assignee: Analogic Corporation, Peabody, Mass.

[21] Appl. No.: 08/986,959

[22] Filed: Dec. 8, 1997

[51] Int. Cl.[6] ........................................ A61B 6/03
[52] U.S. Cl. ............................ 378/19; 378/15; 378/901
[58] Field of Search ................................. 378/15, 19, 901

[56] References Cited

U.S. PATENT DOCUMENTS

| | | | |
|---|---|---|---|
| 4,547,893 | 10/1985 | Gordon | 378/19 |
| 5,671,263 | 9/1997 | Ching-Ming | 378/8 |
| 5,828,718 | 10/1998 | Ruth et al. | 378/19 |
| 5,848,117 | 12/1998 | Urchuk et al. | 378/19 |

Primary Examiner—David P. Porta
Attorney, Agent, or Firm—Lappin & Kusmer LLP

[57] ABSTRACT

A CT scanner includes support means for supporting a radiation source and a detection system in a predetermined spatial relationship and for rotation about a rotation axis, and means for providing relative translation between an object being scanned and the support means as the radiation source and detection system rotate about said rotation axis so as to provide a scan through a predetermined volume of said object. The detection system comprises a plurality of detectors which are offset from a center line passing from the radiation source through the rotation axis, or includes a detection system which is asymmetrically arranged relative to that center line. In the latter case the detectors can be offset or not. Using acquired data, additional projection data is generated preferably through interpolation techniques so as to provide a complete set of data for a predefined slice plane within the scanned volume, which can be subsequently used to back project a tomogram of the object. The complete set of data represents the set of data that would have been generated by the detection system if the offset system had been centered, or the asymmetric system had been symmetric, relative to the center line.

36 Claims, 18 Drawing Sheets

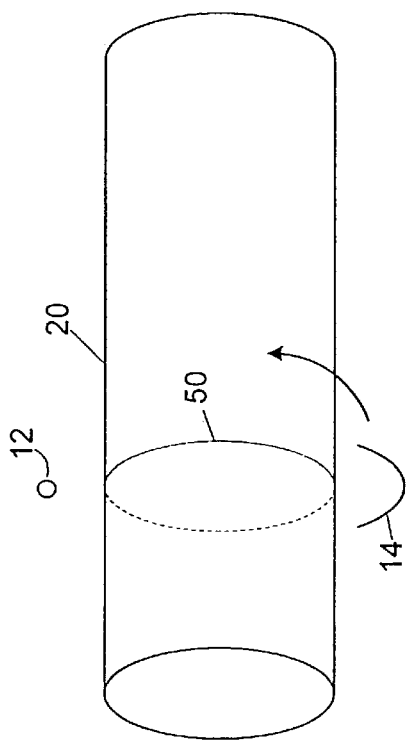
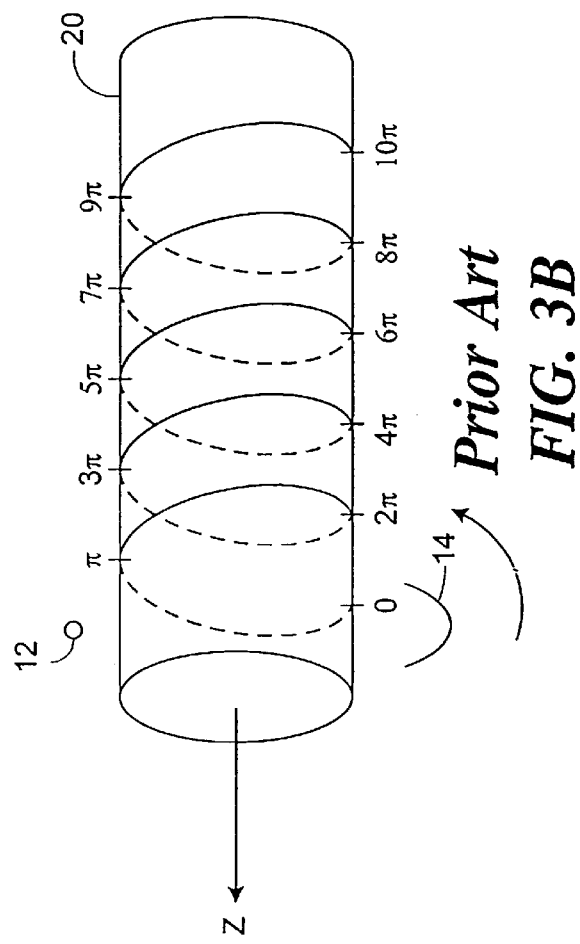
*Prior Art*
*FIG. 3A*
*Prior Art*
*FIG. 3B*

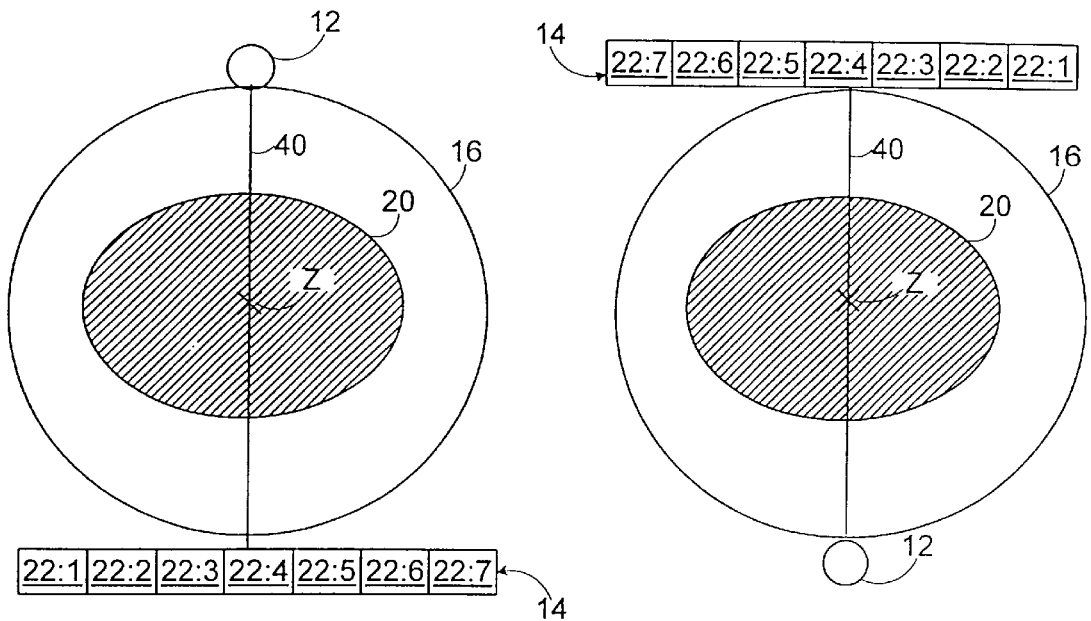
*Prior Art*
FIG. 6A
*Prior Art*
FIG. 6B
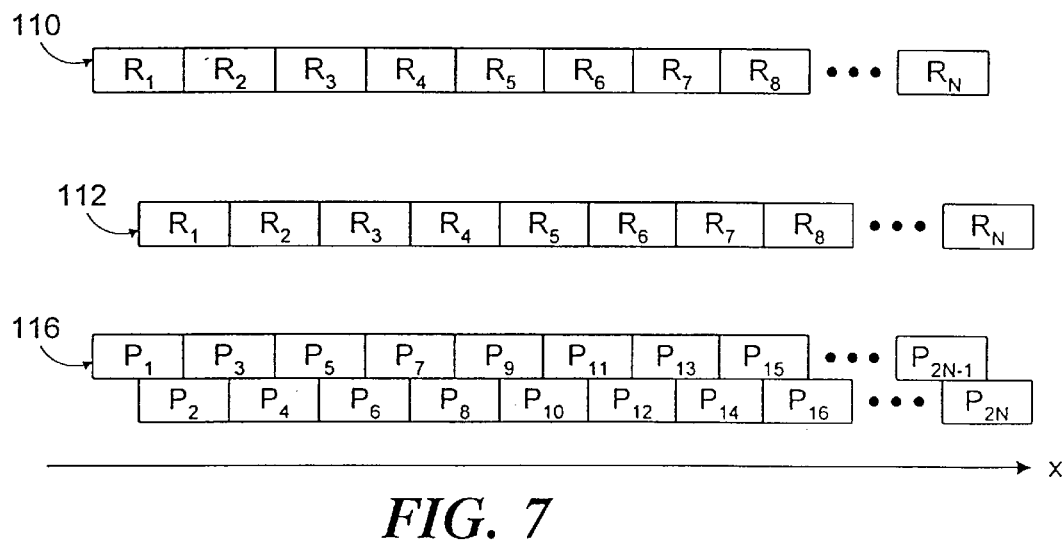
FIG. 7

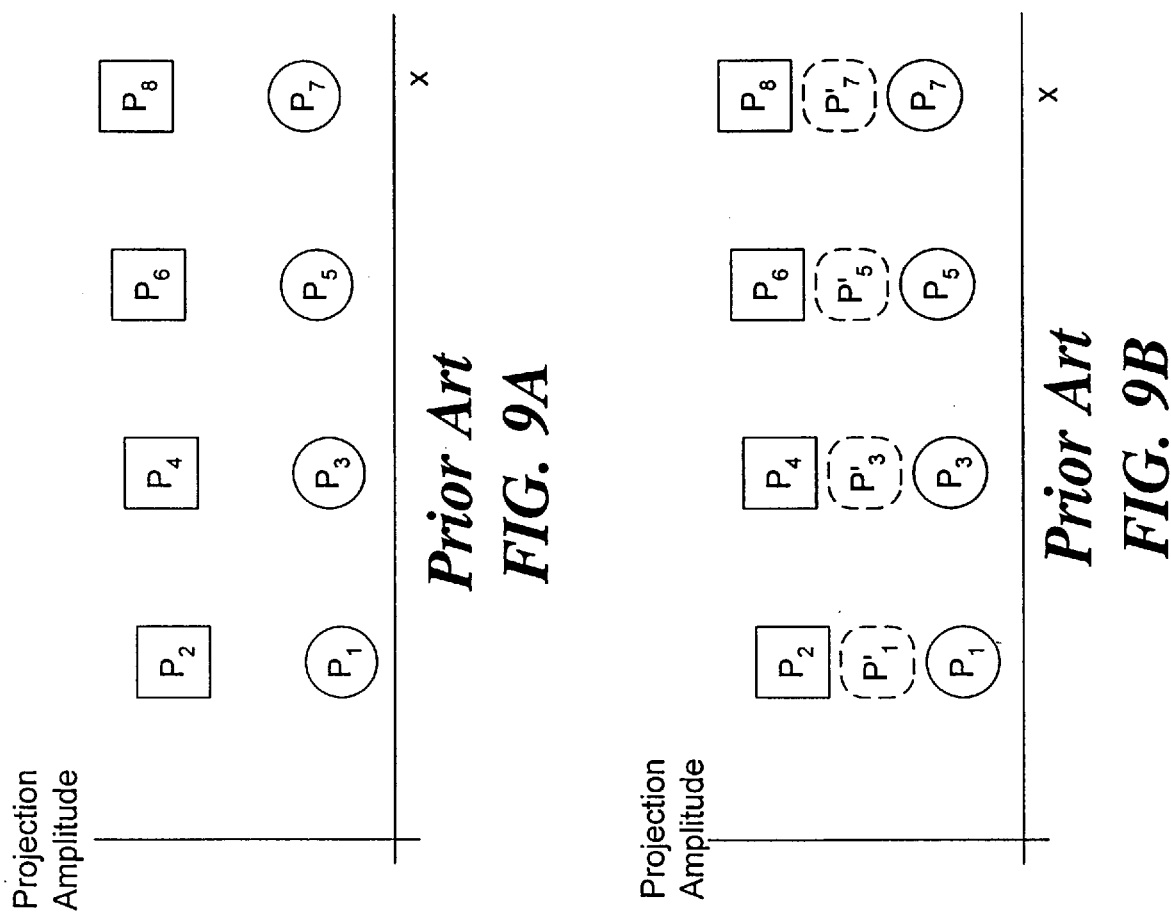

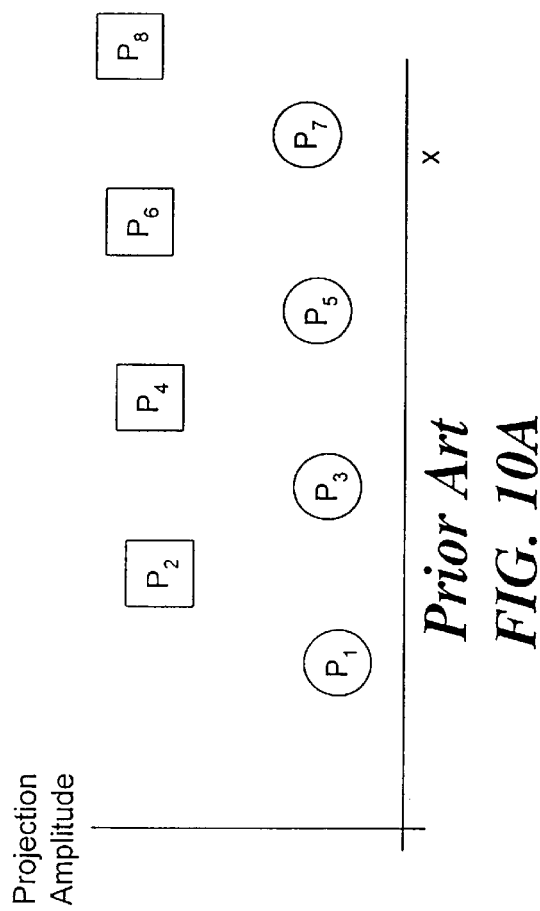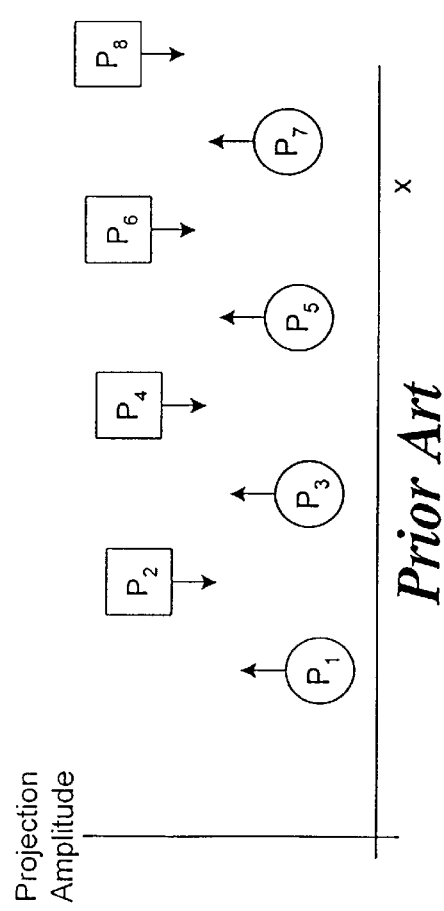

METHOD AND APPARATUS FOR VOLUMETRIC COMPUTED TOMOGRAPHY SCANNING WITH OFFSET SYMMETRIC OR ASYMMETRIC DETECTOR SYSTEM

RELATED APPLICATIONS

This application is related to U.S. application Ser. No. 08/829,062, entitled Improved Method And Apparatus For Helical Computed Tomography Scanning With Asymmetric Detector System, filed Mar. 31, 1997 in the names of Christopher Ruth, John Dobbs and Carl Crawford and assigned to the present assignee; which application is a continuation of U.S. application Ser. No. 08/759,368, entitled Improved Method And Apparatus For Helical Computed Tomography Scanning With Asymmetric Detector System, filed Nov. 27, 1996 in the names of Christopher Ruth, John Dobbs, Carl Crawford and Jan Timmer, now abandoned.

FIELD OF THE INVENTION

The present invention relates generally to volumetric computed tomography scanning. More particularly, the invention relates to an improved method and apparatus for reducing artifacts in tomograms generated from data collected with offset symmetric and asymmetric detector systems during volumetric computed tomography scans.

BACKGROUND OF THE INVENTION

FIG. 1 shows an axial view of a third generation CT scanner 10 that includes an X-ray source 12 and an X-ray detector system 14 secured respectively to diametrically opposite sides of an annular-shaped disk 16. The disk is rotatably mounted within a gantry support (not shown) so that during a scan, the disk continuously rotates about a Z-axis (which is normal to the plane of the page in FIG. 1) while X-rays pass from the source 12 through an object, such as a patient 20, positioned within the opening of the disk to the detector system 14.

The detector system 14 typically includes an array of individual detectors 22 disposed as a single row in the shape of an arc of a circle having a center of curvature at the point 24, referred to as the "focal spot", where the radiation emanates from the X-ray source 12. The X-ray source and the array of detectors are positioned so that the X-ray paths between the source and each detector all lie in a "scanning plane" that is normal to the Z-axis. Since the X-ray paths originate from what is substantially a point source and extend at different angles to the detectors, the X-ray paths form a "fan beam" 26 that is incident on the detector system 14. The X-rays incident on a single detector at a measuring instant during a scan are commonly referred to as a "ray", and each detector generates an output signal indicative of the intensity of its corresponding ray. Since each ray is partially attenuated by all the mass in its path, the output signal generated by each detector is representative of the density of all the mass disposed between that detector and the X-ray source (i.e., the density of the mass lying in the detector's corresponding ray path).

The output signals generated by the X-ray detectors are normally processed by a signal processing portion (not shown) of the CT system. The signal processing portion generally includes a data acquisition system (DAS) which filters the output signals generated by the X-ray detectors to improve their signal-to-noise ratio. One such DAS is described for example in U.S. Pat. No. 4,547,893, which is assigned to the assignee of the present invention, although other systems are known. The filtered output signals generated by the DAS are commonly referred to as "raw data signals". The signal processing portion usually includes a projection filter which logarithmically processes the raw data signals to generate a set of projection data signals so that each projection data signal is representative of the density of the mass lying in a corresponding ray path. The collection of all the projection data signals at a measuring instant or interval is commonly referred to as a "projection" or a "view". The angular orientation of the disk corresponding to a particular projection is referred to as the "projection angle".

FIG. 2 illustrates the orientation of the disk 16 (as well as the X-ray source 12 and detector system 14 mounted to the disk) for generation of a fan beam projection $P_f(\beta)$ at a projection angle of $\beta$. A center line 40, which is used to define reference orientations, extends from the focal spot of the X-ray source 12 through the Z-axis. The projection angle $\beta$ is defined as the angle between a vertical axis and center line 40. Each fan beam projection $P_f(\beta)$ may be represented as a set of data points $F_1, F_2, \ldots, F_N$, where the ith data point $F_i$ represents a sample of the projection data signal generated in response to the ith detector of the detector system 14 at a projection angle of $\beta$, and where the detector system 14 includes N individual detectors.

Each individual detector within detector system 14 has an associated detector angle $\gamma$ that is defined with respect to center line 40. By definition, center line 40 intersects detector system 14 with a detector angle of $\gamma$ equal to 0°. A symmetric detector system 14 (as shown in FIG. 2) extends from a detector angle of $-\gamma_m$ to $+\gamma_m$, and as will be discussed in greater detail below, an asymmetric detector system extends from a detector angle of $-\gamma_m+\alpha$ to $+\gamma_m$. Three of the individual detectors in system 14 are indicated at A, B, and C. Detectors A and B are located at opposite ends of the detector system at detector angles of $-\gamma_m$ and $+\gamma_m$, respectively, and detector C (which is referred to as the central detector) is located at a detector angle of 0°. When the center line 40 intersects the center of the central detector C, the detector system may be described as a "centered" system. Conversely, when the center line 40 intersects the central detector C at a point that is offset from that detector's center, then the detector system may be described as "offset", or as a detector system that is characterized by a detector offset.

During a scan, the disk 16 rotates smoothly and continuously around the object being scanned allowing the scanner 10 to generate a set of fan beam projections $P_f(\beta)$ at a corresponding set of projection angles $\beta$. In a conventional scan, the patient remains at a constant Z-axis position during the scan, whereas in a volumetric (and more specifically described herein as "helical") CT scan, the patient and rotating disk are translated relative to one another along the Z-axis while the disk is rotated about the patient. FIG. 3A schematically illustrates the volume within which the data is collected during a conventional scan, and FIG. 3B illustrates the volume within which the data is collected during a helical scan. As shown in FIG. 3A, if the X-ray source 12 and detector system 14 are rotated about an object 20 while the object 20 remains at a fixed Z-axis location, the rays associated with all the projections collected by detector system 14 will all lie in a common "slice plane" 50. As shown in FIG. 3B, if the object 20 and rotating disk are continuously translated relative to one another in the direction of the Z-axis while the disk is rotated about the object 20, none of the scanning planes associated with the corresponding projections will lie in a common slice plane. Rather, the scanning plane associated with each projection will lie at a unique position along the Z-axis. FIG. 3B illustrates the Z-axis coordinate of the scanning planes corresponding to helical projection angles in the interval $(0,10\pi)$, i.e., five complete rotations of the disk. Since the data values of each projection depend on the Z-axis location of the patient, each projection may be considered as a function of two variables, $\beta$ and z, where $\beta$ represents projection angle and where z represents the Z-axis coordinate of the scanning plane associated with that projection.

Since the patient remains at a constant Z-axis position during a conventional scan, this type of scanning is commonly referred to as "Constant Z-axis position scanning" or CZA scanning. In helical scanning, the projections $P_f(\beta,z)$ are normally acquired such that the Z-axis coordinate z is linearly related to the projection angle $\beta$ so that $z(\beta)=c\beta$, where c is a constant. This form of helical scanning is often referred to as Constant Speed Helical (CSH) scanning.

Using well known algorithms, such as the inverse Radon transform, a tomogram may be generated from a set of projections that all share the same scanning plane, and this common scanning plane is referred to as the "slice plane". A tomogram is representative of the density of a two dimensional "slice", along the slice plane, of the object being scanned. The process of generating a tomogram from the projections is commonly referred to as "filtered back projection" or "reconstruction", since the tomogram may be thought of as being reconstructed from the projection data. The signal processing portion of a CT scanner normally includes a back projector for generating the tomograms from the projections.

In CZA scanning, all the projections share a common scanning plane, so these projections may be applied directly to the back projector for generation of a tomogram. In CSH scanning, each projection has a unique scanning plane located at a unique Z-axis coordinate, so CSH projections may not be applied directly to a back projector. However, as is well known, the data collected during a CSH scan may be interpolated in various fashions to generate a set of interpolated projections that do all share a common scanning plane. Each interpolated projection may be generated by combining two projections taken at equivalent projection angles and at different Z-axis positions. These interpolated projections may be treated as CZA data and may be applied to a back projector to generate a tomogram.

Thus, CSH scanning requires some form of interpolation to generate a tomogram, which is disadvantageous since data interpolated from different Z-axis positions tends to contribute to image artifacts because of inconsistency of the projections from different z positions. Also, since the CSH projection data, which is collected over an interval of Z-axis locations, is combined to generate the interpolated CZA data, tomograms generated during CSH scanning have a wider effective slice plane width than tomograms generated by CZA scanning. However, CSH scanning advantageously permits rapid scanning of a large volume of a patient. For example, in a time interval short enough for a patient to comfortably hold his/her breath (and thereby remain relatively motionless), a CSH scan may collect enough data to fully scan an entire organ such as a kidney. In practice, the disk may, for example, be rotated on the order of $40\pi$ radians (i.e., 20 complete revolutions) during a single helical scan, and the data collected may be used to generate tomograms at a plurality of slice planes.

Fan beam projection data may be applied directly to a back projector that uses a fan beam reconstruction algorithm. However, as is well known, fan beam projection data is often reordered and interleaved to generate parallel beam projection data, and this parallel beam data may be applied to a back projector that uses a parallel beam reconstruction algorithm. FIG. 4A illustrates some of the individual rays used to generate a fan beam projection 100 taken at a fan beam projection angle of zero degrees, and FIG. 4B illustrates some of the individual rays used to generate a parallel beam projection 102 taken at a parallel beam projection angle of zero degrees. As shown, none of the rays in the fan beam projection 100 are parallel to one another, while all of the rays in the parallel beam projection 102 are mutually parallel. Since all of the rays emanate from the focal spot of the X-ray source 12 to form a fan beam, the CT scanner does not generate all the rays of a parallel beam projection simultaneously. However as is well known, the fan beam projection data may be reordered and interleaved to generate parallel beam projections.

FIGS. 5A and 5B illustrate a method of generating a reordered projection. FIGS. 5A and 5B show the positions of X-ray source 12 and detector system 14 during generation of two successive fan beam projections. For ease of illustration, FIGS. 5A and 5B show detector system 14 as including seven individual detectors, 22:1, 22:2, 22:3, 22:4, 22:5, 22:6, and 22:7, although it is well understood that detector systems typically have detectors numbering in the hundreds. As shown, during a scan, X-ray source 12 and detector system 14 rotate in a counter clockwise direction about the Z-axis. During the first fan beam projection, shown in FIG. 5A, a ray 114 is incident on a detector 22:4 (i.e., the detector in the fourth channel of detector system 14). During the next fan beam projection, shown in FIG. 5B, a ray 116 is incident on detector 22:3 (i.e., the detector in the third channel of detector system 14). When the spacing between the individual detectors is matched to the amount of disk rotation between generation of successive fan beam projections, the ray 114 is parallel to, and slightly offset from, ray 116. When this basic relationship is true for all detectors and all fan beam projections, any two rays incident on adjacent detectors during successive fan beam projections are parallel and are slightly offset from each other. In the Anatom scanner, which is manufactured by the assignee of the present invention, the detector system includes three hundred eighty four individual detectors, each of the individual detectors being spaced apart by a detector angle of 0.125°. Consequently, in the Anatom scanner successive fan beam projections are separated by a projection angle that is also equal to 0.125°. This allows the fan beam data collected by that scanner to be reordered into reordered projections, such that the rays used to generate the data points in each reordered projection are all mutually parallel.

Each reordered projection $P_r(\beta)$ has an associated reordered projection angle $\beta$ and may be represented as a set of data points $R_1, R_2, R_3, \ldots, R_N$. Each reordered projection includes the same number of data points as a fan beam projection. The reordered projection angle $\beta$ is the angle between the rays used to generate the data points of the reordered projection and the vertical axis. No two data points in a single reordered projection are generated at the same fan beam projection angle. Rather, each pair of adjacent data points in a reordered projection are generated by adjacent detectors at adjacent fan beam projection angles. So when CSH projection data is reordered into reordered projections, no two data points in a single reordered projection are generated at a common Z-axis position. However, since all the data points in a reordered projection are generated by a set of adjacent fan beam projections, the data points in a reordered projection are generated at Z-axis positions that are relatively proximal to one another.

Each reordered projection $P_r(\beta)$ has an associated reordered projection $P_r(\beta+\pi)$ generated 180° away. These two associated reordered projections are often combined, or interleaved, to generate a single parallel beam projection at a parallel beam projection angle of $\beta$.

In a detector system that is both symmetric and centered, the rays used to generate the reordered projection $P_r(\beta)$ are coincident and antiparallel ("antiparallel" because the relative positions of the detectors and the X-ray source are reversed) with the rays used to generate the associated reordered projection $P_r(\beta+\pi)$. So in the absence of patient motion, the data in the set of reordered projections with $\beta$ in the interval $(0,\pi)$ is identical to the data in the set of reordered projections with $\beta$ in the interval $(\pi,2\pi)$. As is well known, detector offsets are often used to avoid this redundancy and to thereby increase the number of unique sampling points measured with every single complete rotation of the disk. In a detector system that has a detector offset, the rays used to generate the reordered projection $P_r(\beta)$ are parallel to and slightly offset from the rays used to generate the reordered projection $P_r(\beta+\pi)$.

FIGS. 6A and 6B illustrate the spatial relationship between X-ray source 12, a cross section of patient 20, and detector system 14 for projection angles of zero and 180 degrees, respectively. The illustrated detector system 14 is characterized by a quarter detector offset, meaning that the center line 40 intersects the central detector 22:4 at a point that is offset from the center of that detector by one quarter of the detector's width. This detector offset insures that the detector system 14 at 0° is offset from the detector system 14 at 180° by a half detector spacing. In FIGS. 6A and 6B, detector system 14 is once again shown for convenience of illustration as including seven individual detectors.

FIG. 7 illustrates two reordered projections 110, 112 generated from data collected with the quarter detector offset detector system 14, such as shown in FIGS. 6A and 6B, except for N detectors. FIG. 7 also shows a parallel beam projection 116 generated by combining the data in reordered projections 110, 112. In FIG. 7, the X-axis represents the relative linear spatial position of the ray used to generate each data point (i.e., the ray used to generate the data point $R_3$ in projection 110 is to the left of the ray used to generate the data point $R_4$ in projection 110). Reordered projections 110 and 112 are generated at reordered projection angles of 0° and 180°, respectively. Due to the quarter detector offset in detector system 14, the X-axis coordinate of the data point $R_i$ in reordered projection 112 is closer to the X-axis coordinates of the data points $R_i$ and $R_{i+1}$ in the reordered projection 110 than to any other data points in either of projections 110, 112. Although reordered projections 110, 112 are generated 180° apart from one another, the X-axis coordinates of each data point in projection 110 is closer to the coordinates of two data points in projection 112 than to the X-axis coordinates of any other data point in projection 110. This relationship allows any two reordered projections generated 180° apart to be interleaved to generate a single parallel beam projection.

Parallel beam projection 116 is formed by combining or interleaving the data in reordered projections 110, 112. Parallel beam projection 116 includes a set of data points $P_i$ for all integers i from one to 2N. So parallel beam projection 116 includes twice as many data points as any of the single reordered projections 110, 112. In parallel beam projection 116, the odd data point $P_{2i+1}$ equals the data point $R_{i+1}$ in reordered projection 110, and the even data point $P_{2i+2}$ equals the data point $R_{i+1}$ in reordered projection 112 for all integers i from zero to N minus 1. So in parallel beam projection 116, all of the odd data points (e.g., $P_1$ and $P_3$) are contributed by reordered projection 110 and all of the even data points (e.g., $P_2$ and $P_4$) are contributed by reordered projection 112.

FIGS. 8A, 8B, and 8C show graphs that illustrate the relationship between the fan beam projection angle and the parallel beam projection angle of data points in interleaved parallel beam projections generated by a symmetric offset detector array. More specifically, these figures illustrate how fan beam projections for fan beam projection angles in the interval $(0, 2\pi)$ may be reordered and interleaved to generate a set of interleaved parallel beam projections for parallel beam projection angles in the interval $(-\pi/2, \pi/2)$. As is well known, back projectors using parallel beam filtered back projection algorithms may generate tomograms from parallel beam projections with parallel beam projection angles in the interval $(-\pi/2, \pi/2)$.

FIG. 8A shows a graph that illustrates the relationship between reordered and fan beam projection angles. In FIG. 8A, the Y-axis represents reordered projection angle and the X-axis represents fan beam projection angle. The two lines indicated at A represent the data collected by detector A (as shown in FIG. 2), which is located at a detector angle of $-\gamma_m$; the two lines indicated at B represent data collected by detector B, which is located at a detector angle of $\gamma_m$; and the two lines indicated at C represent data collected by the central detector C, which is located at a detector angle of 0°. Since detectors A and B are located at opposite ends of the detector system, any horizontal line extending from line A to line B represents the data in a single reordered projection. Similarly, any vertical line extending from line A to line B represents the data in a single fan beam projection. For example, horizontal line 130 represents the data in a reordered projection for a reordered projection angle of $\pi/2$. The reordered projection indicated by line 130 is formed by data collected at fan beam projection angles in the continuous interval $(\pi/2-\gamma_m, \pi/2+\gamma_m)$ equal to the angle subtended by the fan beam between the lines A and B. Most reordered projections may similarly be formed from data collected over a continuous interval of fan beam projections. However, all the reordered projections for reordered projection angles in the range $(-\gamma_m, \gamma_m)$ are formed from data collected over two non-adjacent intervals of fan beam projection angles. For example, a reordered projection for a reordered projection angle of 0° is formed by data collected by the detectors between detectors C and B over fan beam projection angles in the interval $(0, \gamma_m)$, and also from data collected by the detectors between detectors A and C over fan beam projection angles in the interval $(2\pi-\gamma_m, 2\pi)$. So the reordered projections for reordered projection angles in the range $(-\gamma_m, \gamma_m)$ are formed from some data collected at the beginning of a disk rotation (i.e., near fan beam projection angle of 0°), and from some data collected near the end of a disk rotation (i.e., near fan beam projection angle of $2\pi$).

FIG. 8B shows a graph that is equivalent to the graph shown in FIG. 8A, however, in FIG. 8B, the Y-axis represents parallel beam projection angles rather than reordered projection angles. Since each parallel beam projection is formed by combining data from two reordered projections, the parallel beam projection angles represented by the Y-axis in FIG. 8B only extend over the interval $(-\pi/2, \pi/2)$ rather than over the interval $(-\pi, \pi)$. In FIG. 8B, the data collected by detector A over fan beam projection angles in the intervals $(0, \pi/2-\gamma_m)$, $(\pi/2-\gamma_m, 3\pi/2-\gamma_m)$, and $(3\pi/2-\gamma_m, 2\pi)$ are represented by lines A', A, and A", respectively. The data collected by detector C over fan beam projection angles in the intervals $(0, \pi/2)$, $(\pi/2, 3\pi/2)$, and $(3\pi/2, 2\pi)$ are represented by lines C', C, and C", respectively. The data collected by detector B over fan beam projection angles in the intervals $(0, \pi/2+\gamma_m)$, $(\pi/2+\gamma_m, 3\pi/2+\gamma_m)$, and $(3\pi/2+\gamma_m, 2\pi)$ are represented by lines B', B, and B", respectively.

FIG. 8C shows a graph that indicates how the data shown in FIG. 8B may be interleaved to generate interleaved parallel beam projections. The data indicated at lines B' and B" are interleaved with the data indicated at line A, the data indicated at lines C' and C" are interleaved with the data indicated at line C, and the data indicated at lines A' and A" are interleaved with the data indicated at line B. So when forming parallel beam projections, the data from the central detector C is interleaved with other data collected by the central detector (as indicated by C' and C"). However, the central detector is the only detector in the system to have this property. Each remaining detector is interleaved with a detector on the opposite side of the detector system to generate the parallel beam projections. For example, the data collected by detector A is interleaved with data collected by detector B to form a parallel beam projection. In FIG. 8C, interleaved parallel beam projections are represented by horizontal lines. For example, line 132 represents the data in the parallel beam projection at the parallel beam projection angle of $\pi/4$.

In an interleaved parallel beam projection, the ray path used to generate the ith data point $P_i$ is closer to the ray paths used to generate the adjacent data points $P_{i-1}$ and $P_{i+1}$ than to any other ray paths. However, the difference between the measurement times of adjacent data points (e.g., $P_i$ and $P_{i-1}$) is much greater than the difference between the measurement times of alternate data points (e.g., $P_i$ and $P_{i-2}$). For example, if $T_i$ represents the time that a data point $P_i$ is measured, then $T_i$ minus $T_{i-1}$ is much greater than $T_i$ minus $T_{i-2}$. This is true because all of the even points of a single parallel beam projection are contributed by a single reordered projection (and all the data points of a reordered projection are generated by a set of adjacent fan beam projections). However, adjacent data points in the parallel beam projection are contributed by two different reordered projections generated 180° apart from one another. So the measurement times of such adjacent data points are separated by the time required for the disk to rotate approximately 180°.

In the absence of patient motion (i.e., in a CZA scan during which the patient does not move) the portions of the patient measured by adjacent data points in a parallel beam projection are proximal to one another. However, in a parallel beam projection generated from CSH data, the portions of the patient measured by adjacent data points are axially separated by a relatively large distance because the relative movement of the patient and the rotating disk is a translation of a considerable distance during the time required for the disk to rotate approximately 180°. This leads to a discrepancy between the even data points and the odd data points in every single parallel beam projection generated during a CSH scan. These discrepancies appear as high frequency noise in the projection data and complicate the process of generating tomograms from CSH data.

FIGS. 9A and 9B illustrate one prior art method for generating a tomogram from CSH data generated by a symmetric centered detector system. FIG. 9A shows a graph of some of the data points in a single interleaved parallel beam projection generated by a symmetric centered detector system during a CSH scan at a parallel beam projection angle of $\beta$. In FIG. 9A, the Y-axis represents the amplitude of the data points of the projection, and the X-axis represents the relative linear spatial position of the rays used to generate the data points of the projection. Since the illustrated projection was generated using a centered detector system, the rays used to generate the data points $P_1$ and $P_2$ (which are 180° apart) are coincident, so these data points share the same X-axis coordinate. Since the illustrated projection was generated during a CSH scan, there tends to be a discrepancy between the amplitudes of the odd data points and the even data points. As was stated above, this discrepancy occurs because the odd data points are generated at Z-axis locations that are displaced from the Z-axis locations where the even data points are generated.

In a typical CSH scan, the collected data is used to generate a tomogram at a slice plane having a Z-axis location $z_{sp}$. Although the odd and even data points in each parallel beam projection are all generated at slightly different Z-axis locations, all of the odd data points are typically generated on one side of the slice plane, and similarly, all of the even data points are generated on the other side of the slice plane, i.e., the slice plane is positioned along the Z-axis between the two sets of odd and even data points. Interpolation is normally performed between each pair of corresponding data points displaced 180° to estimate the value of a projection at the location of the slice plane $z_{sp}$. FIG. 9B illustrates the results of this type of interpolation. As shown, the value of an interpolated data point $P'_1$ at the slice plane is generated by averaging the data points $P_1$ and $P_2$, the value of an interpolated data point $P'_3$ at the slice plane is generated by averaging the data points $P_3$ and $P_4$, and so on. The interpolated data points, which are all illustrated as dashed-circles, represent a non-interleaved parallel beam projection at the slice plane $z_{sp}$ for a projection angle of $\beta$. Similar interpolations are performed for every pair of parallel beam projections at projection angles 180° apart for each parallel beam projection angle $\beta$ and the associated $\beta+180°$, and then the interpolated parallel beam projections are filtered and applied to a back projector for generation of a tomogram. It is not necessary to perform further interpolation on the parallel beam projections. The interpolation coefficient for each data point at a projection angle can be treated as a weighting factor for that data point, and the weighting factor can be applied to the original data point in the fan beam projection. In this way, the interpolation to the slice plane $z_{sp}$ is performed up-front in the fan beam projection by weighting each data point according to its Z-axis position. It is not necessary to reorder the data into parallel beam projections either. The tomogram can be generated from the weighted fan beam projections by using a fan beam filtered back-projection.

FIG. 10A shows an example of a graph of some of the data points in a single interleaved parallel beam projection generated by a symmetric offset detector system during a CSH scan at a parallel beam projection angle of $\beta$. Since the detector system is characterized by an offset, each data point in the projection has a unique X-axis coordinate position, and the odd data points are interleaved with the even data points along the X-axis. Prior art methods of generating tomograms from such data normally involve performing an interpolation by weighting the original fan beam projection data similar to the methods discussed above in connection with FIGS. 9A and 9B. Each original data point is multiplied by a weighting factor and thereby shift the amplitude values of the odd and even data points towards each other as illustrated in FIG. 10B. These weighted original data points may then be used to generate the tomogram by a fan beam filtered backprojection. During the backprojection, the weighted data from fan beam projection at 180° apart are superimposed such that it is almost equivalent to having data interpolated to the slice plane position. The weighted original data can also be reordered into parallel beam projections for a parallel beam filtered backprojection. In this method, the filtering process of convolution performs some degree of averaging for adjacent even and odd points such that the weighting in the original data is almost equivalent to having even and odd data points in the interleaved parallel beam projection interpolated to the slice plane.

In every pair of corresponding original data points (e.g., $P_1$ and $P_2$), one of the data points is generated at a first set of X and Z-axis coordinates ($x_1$, $z_1$) and the other data point is generated at a second set of X and Z-axis coordinates ($x_2$, $z_2$). The weighting factors are selected so as to generate an equivalent interpolated data point having a Z-axis coordinate at the slice plane $z_{sp}$. However, these prior methods do not fully deal with the fact that the two original data points are generated at different X-axis coordinates. The weighting factor w ranges from 0.0 to 1.0. When the weighted data are reordered into an interleaved parallel beam projection, the projection amplitudes between adjacent data points can be huge because the even and odd data points have been multiplied by w and 1−w, respectively. The normal filter for convolution and the backprojection can reduce, but not completely remove, the amplitude differences between the even and odd data points. Consequently, the tomogram may contain a relatively large amount of artifacts due to the large amplitude differences between even and odd data points. It is possible to remove these artifacts by using a filter with a lower frequency response. But, by doing so, the spatial resolution of the tomogram is reduced. By the time these artifacts are fully removed, the spatial resolution is degraded to the level as if the data were collected and processed without the offset in the detector system. In the same situation, if the tomogram is generated from the weighted data by fan beam filtered backprojection method, the spatial resolution must be reduced to avoid these weighting induced artifacts. Again, the higher resolution advantage of an offset detector system will be lost by the time these artifacts are completely removed. There is therefore a need for an improved method of processing the data collected by an offset detector system for a CSH scan.

Another problem with prior art helical scanning techniques relates to use of asymmetric detector systems. FIG. 11 illustrates the geometry of a CT scanner having an asymmetric detector system 14. This detector system includes a symmetric portion 14a extending from detector angle $-\gamma_m+\alpha$ to $\gamma_m-\alpha$, and an asymmetric portion 14b extending from detector angle $\gamma_m-\alpha$ to $\gamma_m$, where $\alpha$ is the angular extent of the asymmetric portion. Detector system 14 may also be thought of as not including a portion 14c extending from detector angle $-\gamma_m$ to $-\gamma_m+\alpha$. If detector system 14 did include the missing portion 14c, then the detector system would be symmetric.

Such asymmetric detector systems are often used in CT scanners so as to increase the "field of view" (FOV) of the scanner without significantly increasing the cost of the detector system and associated DAS. The FOV of a scanner is determined by the effective angular extent of the detector system. For example, without rotation the angular extent of a scanner (i.e., the angle subtended by the fan beam) using the symmetric detector system illustrated in FIG. 2 is equal to $2\gamma_m$, and the angular extent of a scanner (i.e., the angle subtended by the fan beam) using the asymmetric detector system illustrated in FIG. 11 is equal to $2\gamma_m-\alpha$. But with rotation of the detector system over 360 degrees during a scan, both give effective angular extent of $2\gamma_m$. So use of the asymmetric detector system achieves the same FOV as the symmetric detector system and saves the detectors over the angle $\alpha$. As is well known, the importance of each detector (in terms of its contribution to tomograms) decreases with increasing detector angle. So it is reasonable to eliminate half the detectors beyond a certain detector angle and thereby generate an asymmetric detector system. By way of example, the above-referenced Anatom scanner uses an asymmetric detector system where $\gamma_m$ is equal to 28.85°, and $\alpha$ is equal to 9.69°. Although such asymmetric detector system are popular, their use complicates the process of generating helical scans.

FIG. 12 illustrates the X-axis coordinates of the data points in two reordered projections 210, 212, and also of two parallel beam projections 214, 216. Projections 210, 212, 214, and 216 are generated from data collected by an asymmetric offset detector system 14 (as shown in FIG. 11) that includes N individual detectors. The asymmetric portion 14b of detector system 14 is assumed to include j individual detectors, and the symmetric portion 14a therefore includes N−j individual detectors.

Each of the reordered projections 210, 212 includes N data point $R_k$ for all integers k from one to N. Reordered projection 210 is generated at a reordered projection angle of $\beta$, and reordered projection 212 is generated at a reordered projection angle of $\beta+\pi$, so these projections may be combined to generate a parallel beam projection. In reordered projection 210, the data points $R_1$ through $R_j$ are generated by the asymmetric portion 14b, and the data points $R_{j+1}$ through $R_N$ are generated by the symmetric portion 14a. In reordered projection 212, the data points $R_1$ through $R_{N-j}$ are generated by the symmetric portion 14a, and the data points $R_{N-j+1}$ through $R_N$ are generated by the asymmetric portion 14b. The data points collected by the symmetric portion 14a of the detector system (i.e., data points $R_{j+1}$ to $R_N$ in projection 210, and data points $R_1$ to $R_{N-j}$ in projection 212) may be interleaved to generate a parallel beam projection. However, as illustrated in FIG. 11, no data points are available for interleaving the data points collected by the asymmetric portion 14b. Such data points could only have been collected by the missing portion 14c of the detector system 14. It is this inability to interleave the data collected by the asymmetric portion 14b that complicates the process of CSH scanning with an asymmetric detector system.

Parallel beam projection 214 is generated by combining the reordered projections 210, 212. Since no data points are available for interleaving the data collected by the asymmetric portion 14b of the detector system 14, parallel beam projection 214 includes a central interleaved portion and two exterior non-interleaved portions. More specifically, parallel beam projection 214 includes an exterior region composed of data points $P_1$ to $P_j$, and these data points are equal to the data points $R_1$ to $R_j$, respectively, of reordered projection 210. Parallel beam projection 214 also includes an exterior region composed of data points $P_{2N-j+1}$ to $P_{2N}$, and these data points are equal to the data points $R_{N-j+1}$ to $R_N$, respectively, of reordered projection 212. Finally, parallel beam projection 214 includes a central interleaved portion composed of data points $P_{j+1}$ to $P_{2N-j}$, and these data points are generated by combining the data points $R_{j+1}$ to $R_N$ from reordered projection 210 and the data points $R_1$ to $R_{N-j}$ from reordered projection 212. More specifically, the data point $P_{j+1}$ equals the data point $R_{j+1}$ from projection 210, the data point $P_{j+2}$ equals the data point $R_1$ from projection 212, the data point $P_{j+3}$ equals the data point $R_{j+2}$ from projection

210, the data point $P_{j+4}$ equals the data point $R_2$ from projection 212, and so on. Since the data points in the exterior regions of the parallel beam projection are not interleaved, the spacing between adjacent data points in these regions is double the spacing between adjacent data points in the central region.

Parallel beam projection 216 includes exactly the same data as parallel beam projection 214. However, the indices in parallel beam projection 216 have been altered to reflect the difference in the spacing between data points in the exterior regions and in the central region. More specifically, in parallel beam projection 216, the indices of the data points have been altered so as to eliminate even data points from one of the exterior (non-interleaved) regions and to eliminate odd data points from the other exterior region. The odd data points $P_1, P_3, \ldots, P_{2j-1}$, form one of the exterior regions of projection 216, and these data points are of course equal to the data points $P_1$ to $P_j$, respectively, of projection 214. Similarly, the even data points $P_{2N+2}, P_{2N+4}, \ldots, P_{2N+2j}$, form the other exterior region of projection 216, and these data points are equal the data points $P_{2N-j+1}$ to $P_{2N}$, respectively, of projection 214. Finally, the even and odd data points $P_{2j+1}$ to $P_{2N}$ form the central (interleaved) region of projection 216, and these data points are equal to the data points $P_{j+1}$ to $P_{2N-j}$, respectively, of projection 214. The representation for the data points used in parallel beam projection 216 is convenient since in this projection, all the odd data points are contributed by one of the reordered projections (i.e., projection 210) and all the even data points are contributed by the other reordered projection (i.e., projection 212). Further, in projection 216, the spacing between any two data points can be calculated as a simple function of the indices of the data points.

Prior art helical scanning techniques do not work well when applied to parallel beam projections collected by an asymmetric detector system such as projection 216. Interpolation may be performed on the interleaved data points in the central region of such projections to generate data points at the slice plane. However, since the data in the exterior regions is not interleaved, this data may not be interpolated to generate data points at the slice plane. There is therefore a need for a CSH scanning technique that generates tomograms from projections collected by asymmetric offset detector systems.

OBJECTS OF THE INVENTION

It is an object of the present invention to substantially reduce or overcome the above-identified problems of the prior art.

Another object of the present invention is to provide an improved method and apparatus for generating tomograms from CSH data collected with an offset detector system.

Yet another object of the present invention is to provide an improved method and apparatus for generating tomograms from CSH data collected with an asymmetric detector system.

Still another object of the present invention is to provide an improved method and apparatus for generating tomograms from CSH data collected with an asymmetric offset detector system.

And yet another object of the present invention is to provide an improved interpolation system for generating interpolated CZA projections from CSH projections while preserving the information collected by an offset detector system for achieving higher spatial resolution.

And still another object of the present invention is to provide an improved parallel beam converter for generating fully interleaved parallel beam projections from CSH data collected by an asymmetric offset detector system.

And yet another object of the present invention is to provide an improved method and apparatus for smoothing discontinuities across symmetry boundaries in fully interleaved parallel beam projections generated from CSH data collected by an asymmetric offset detector system.

SUMMARY OF THE INVENTION

These and other objects are provided by an improved interpolation system for generating interpolated CZA projections from CSH projection data collected by an offset detector system. The interpolation system may generate at least some of the data points in the interpolated CZA projections according to estimates of data points that would have been generated by detectors in a centered detector system. The invention also provides an improved parallel beam converter for generating fully interleaved parallel beam projections from CSH data collected with an asymmetric offset detector system. Further, the invention provides a symmetry boundary adjuster for smoothing discontinuities in the fully interleaved parallel beam projections.

Still other objects and advantages of the present invention will become readily apparent to those skilled in the art from the following detailed description wherein several embodiments are shown and described, simply by way of illustration of the best mode of the invention. As will be realized, the invention is capable of other and different embodiments, and its several details are capable of modifications in various respects, all without departing from the invention. Accordingly, the drawings and description are to be regarded as illustrative in nature, and not in a restrictive or limiting sense, with the scope of the application being indicated in the claims.

BRIEF DESCRIPTION OF THE DRAWINGS

For a fuller understanding of the nature and objects of the present invention, reference should be had to the following detailed description taken in connection with the accompanying drawings in which the same reference numerals are used to indicate the same or similar parts wherein:

FIG. 3A illustrates in a simplified schematic drawing the slice plane of the projection data collected during a CZA scan;

FIG. 3B illustrates in a simplified schematic drawing the slice planes of the projections collected during a CSH scan;

FIGS. 6A and 6B illustrate in a simplified schematic form the spatial relationship between the X-ray source, the patient, and the detector system with a quarter detector offset of a prior art CT scanner at projection angles of 0° and 180°, respectively;

FIG. 7 illustrates in simplified form, the spatial relationship of the X-axis coordinates of data points in two reordered projections generated at 0° and 180°, and also illustrates the spatial relationship of the X-axis coordinates of data points in a parallel beam projection generated from those two reordered projections;

FIG. 9A shows a simplified graph of some data points in a parallel beam projection generated from data collected during a CSH scan by a centered detector system;

FIG. 9B illustrates in the form of a simplified graph, a prior art method of generating an interpolated CZA projection from the data points shown in FIG. 9A;

FIG. 10A shows a simplified graph of some data points in a parallel beam projection generated from data collected during a CSH scan by an offset detector system;

FIG. 10B illustrates in the form of a simplified graph a prior art method of generating an interpolated CZA projection from the data points shown in FIG. 10A;

DETAILED DESCRIPTION OF THE DRAWINGS

Figure 13:
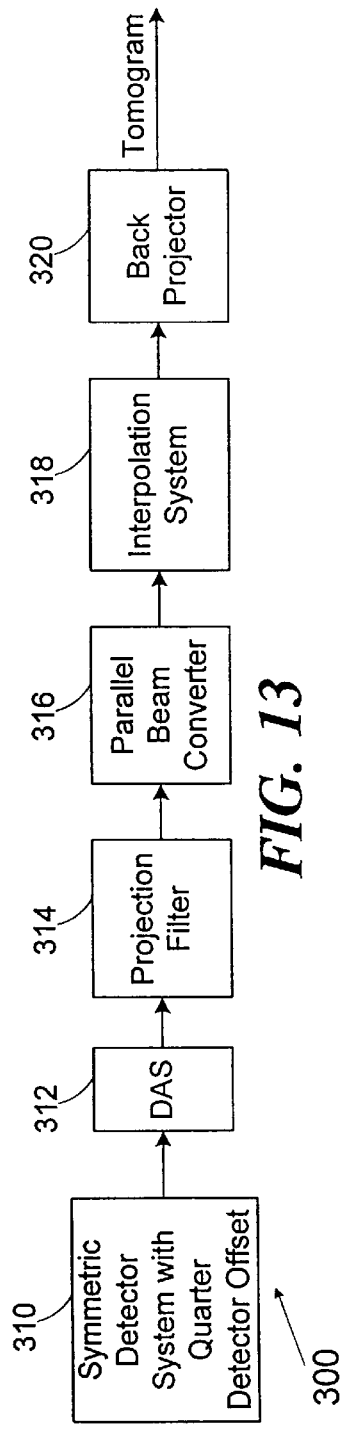
FIG. 13 shows a block diagram of a portion of a CT scanner constructed according to the invention.

FIG. 13 shows a simplified block diagram of one embodiment of a CT scanner 300 constructed according to one aspect of the invention. Scanner 300 may be used to generate tomograms of improved quality from CSH scans. Scanner 300 includes a symmetric offset detector system 310, a DAS 312, a projection filter 314, a parallel beam converter 316, an improved interpolation system 318, and a back projector 320. In the illustrated embodiment, symmetric detector system 310 is characterized by a quarter detector offset, however, those skilled in the art will appreciate that other amounts of detector offset may be used with the invention.

During a CSH scan, the output signals generated by the detector system 310 are applied to DAS 312 which generates therefrom the raw data signals. Projection filter 314 receives the raw data signals and generates therefrom the fan beam projections. Parallel beam converter 316 receives the fan beam projections, and reorders and interleaves them to generate interleaved parallel beam projections. Interpolation system 318 receives the parallel beam projections and generates therefrom interpolated CZA parallel beam projections. Back projector 320 receives the interpolated CZA parallel beam projections and generates therefrom a tomogram.

Scanner 300 generates a tomogram from fan beam projections collected for helical projection angles in the range $(x-2\gamma_m, 2\pi+x+2\gamma_m)$. Scanner 300 uses this data to generate a tomogram having a Z-axis coordinate $z_{sp}$ corresponding to the helical projection angle $x+\pi$. So with reference to FIG. 3B, where $x=2\pi$ scanner 300 may use the data collected over helical projection angles in the range $(2\pi-2\gamma_m, 4\pi+2\gamma_m)$ to generate a tomogram having a slice plane, or Z-axis coordinate $z_{sp}$, corresponding to the helical projection angle $3\pi$. As will be discussed in greater detail below, the tomograms generated by scanner 300 are characterized by improved resolution and reduced artifacts as compared with tomograms generated by prior art helical scanners. As will be more evident hereinafter, the tomograms generated by scanner 300 preserve the information collected by the offset detector system rather than treating this data as if it were collected by a centered detector system as has been done in the prior art.

Figure 14B:
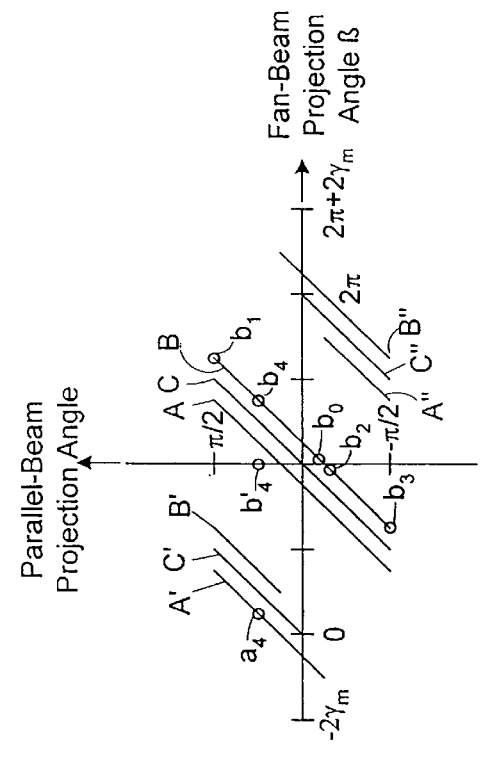
FIGS. 14A, 14B, and 14C graphically illustrate a method according to one aspect of the invention for generating interleaved parallel beam projections with parallel beam projection angles in the range $(-\pi/2, \pi/2)$ from fan beam projections with fan beam projection angles in the range $(-2\gamma_m, 2\pi+2\gamma_m)$ collected by an offset detector system during a CSH scan.
Figure 14C:
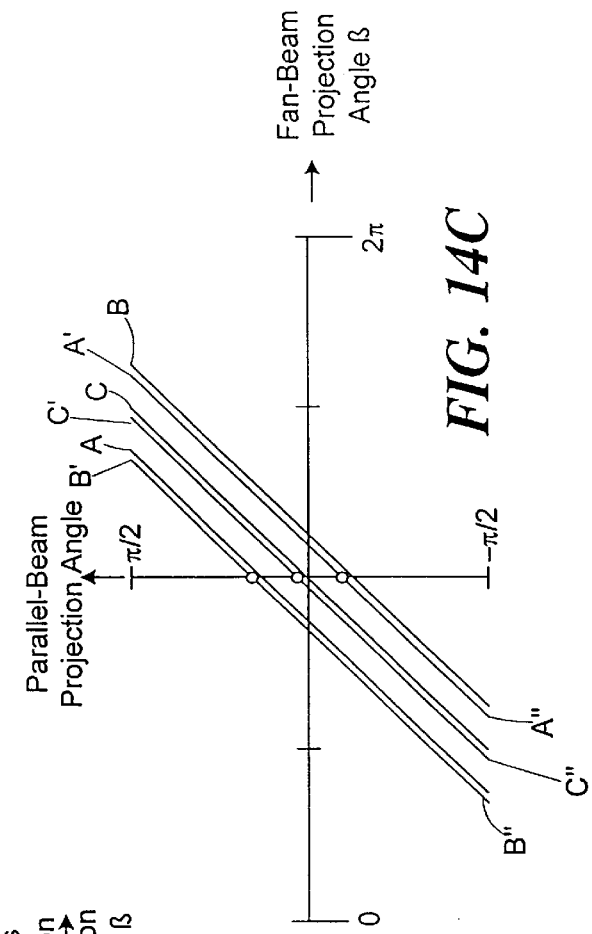
Figure 14A:
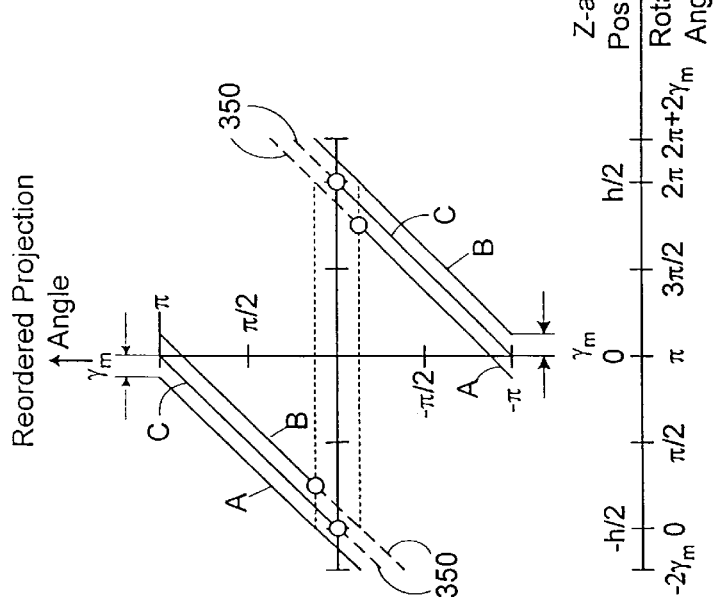

FIGS. 14A, 14B, and 14C illustrate the operation of parallel beam converter 316. FIG. 14A illustrates fan beam projection data collected by scanner 300 during a CSH scan for fan beam projection angles in the interval ($-2\gamma_m$, $2\pi+2\gamma_m$), and also illustrates the Z-axis coordinate of the scanning plane for each of the fan beam projections. Parallel beam converter 316 reorders and interleaves this data to generate parallel beam projections for parallel beam projection angles in the interval ($-\pi/2, \pi/2$) as shown in FIG. 14C. Scanner 300 then uses this parallel beam projection data to generate a tomogram at a slice plane $z_{sp}$ corresponding to a fan beam projection angle of $\pi$. As indicated in FIG. 14A, the relative distance a patient is translated is a distance h along the Z-axis during the time required for the disk to rotate 360°. The distance h may be referred to as the "pitch" of the helical scan.

Figure 8A:
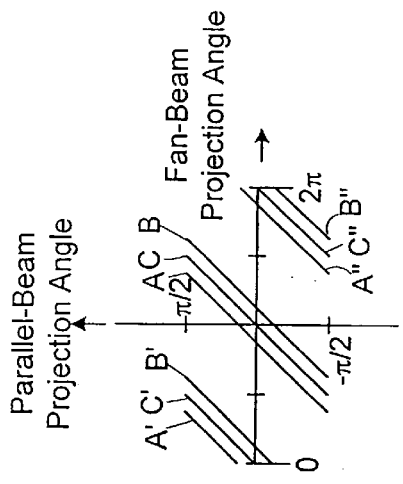
FIGS. 8A, 8B, and 8C graphically illustrate a prior art method of reordering and interleaving fan beam projections collected for fan beam projection angles in the interval $(0,2\pi)$ into parallel beam projections with parallel beam projection angles in the interval $(-\pi/2,\pi/2)$.
Figure 8B:
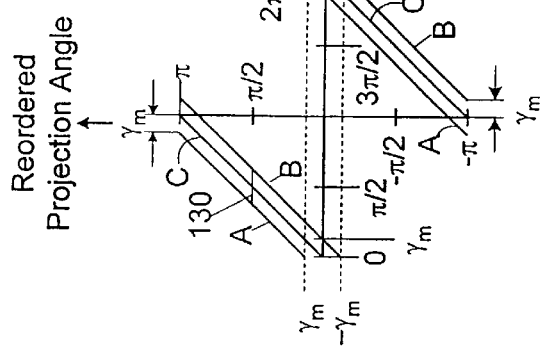
Figure 8C:
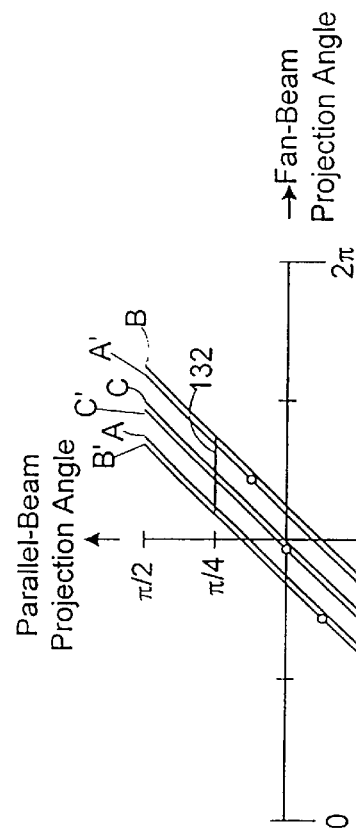

Comparing FIGS. 8A–8C with FIGS. 14A–14C, it is evident that parallel beam converter 316 does not generate the parallel beam projections in the same manner as in CZA scanning. In CZA scanning, in FIG. 8C fan beam projections for fan beam projection angles in the interval (0, $2\pi$) were reordered and interleaved to generate parallel beam projections for parallel beam projection angles in the interval ($-\pi/2, \pi/2$). As described more fully below, parallel beam converter 316 of the present invention uses an extra $4\gamma_m$ (equivalent to two fan angles of the detector system) of fan beam projection data to generate the parallel beam projections.

Figure 1:
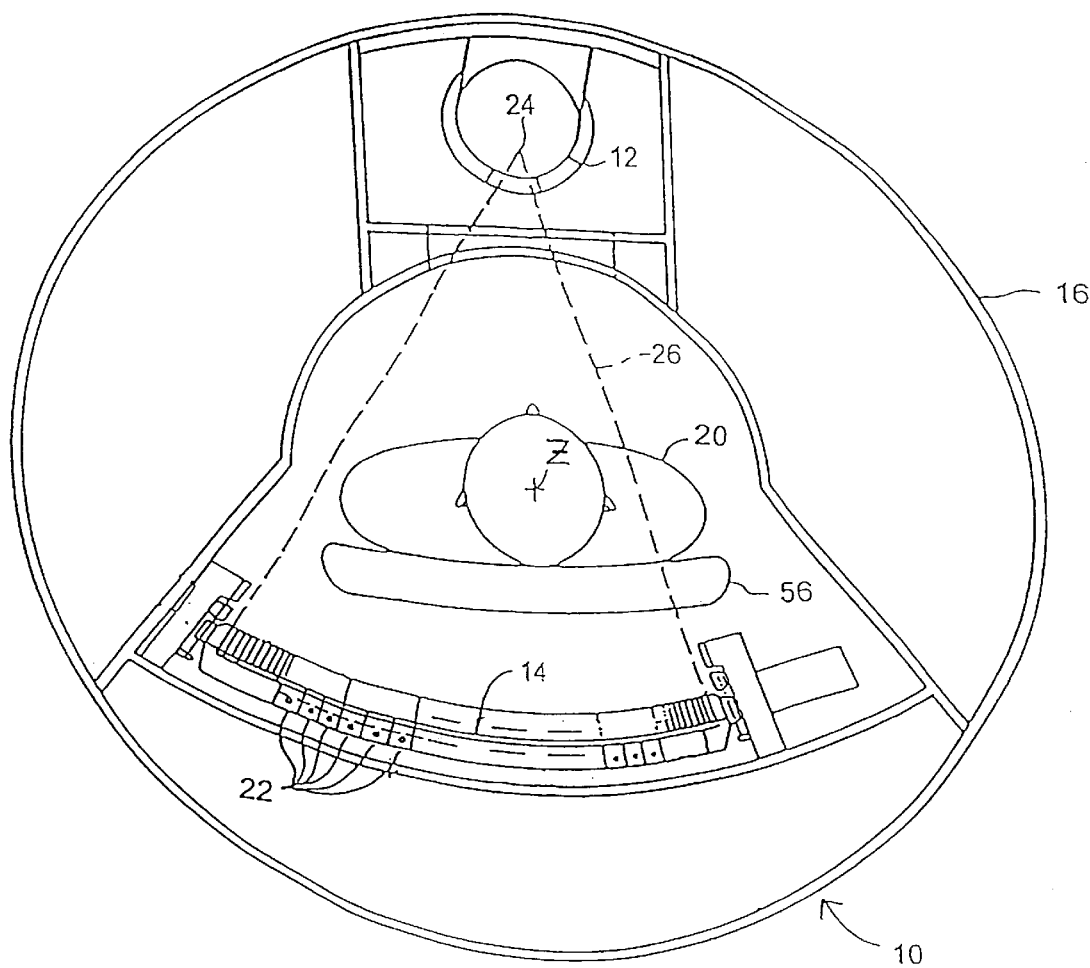
FIG. 1 shows an axial view of a prior art CT scanner.
Figure 2:
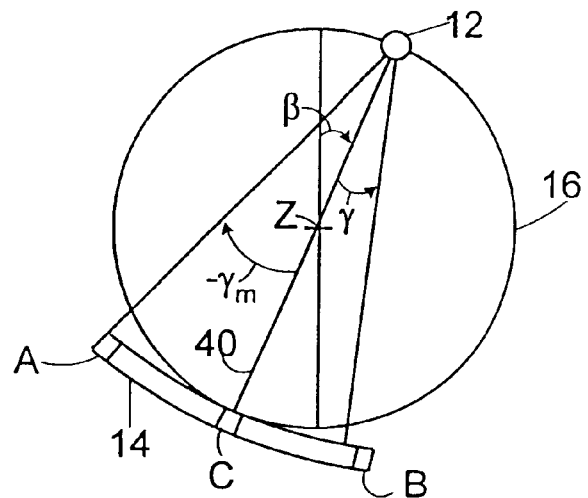
FIG. 2 shows an axial view of a prior art CT scanner with a symmetric detector system.

The reason parallel beam converter 316 uses this extra $4\gamma_m$ of fan beam projection data is illustrated in FIG. 14B. In FIG. 14B, lines B', B, and B" represent data collected by detector B (as shown in FIG. 2). The line B is shown as broken into a first line segment $b_0b_1$ and a second line segment $b_2b_3$. The line segment $b_0b_1$ represents data collected by the detector B on one side of the slice plane (corresponding to a fan beam projection angle of $\pi$), and the line segment $b_2b_3$ represents data collected by the detector B on the other side of the slice plane. Scanner 300 uses the data on line segment $b_0b_1$ with data collected by detector A on the other side of the slice plane to generate interpolated data points at the slice plane. The data available for this interpolation is provided by the data indicated at line A'. For example, scanner 300 combines the data points $b_4$ and $a_4$ to generate an interpolated data point $b'_4$ at the slice plane. Similarly, the data in line segment $b_2b_3$ is combined with the data in line A" to generate interpolated data points at the slice plane. To provide sufficient data for generation of an interpolated data point corresponding to every data point in line segment $b_0b_1$, the line A' preferably extends to a fan beam projection angle of $-2\gamma_m$ as shown in FIG. 14B. Similarly, line B" preferably extends to a fan beam projection angle of $2\pi+2\gamma_m$ so as to provide adequate data for generating interpolated data points corresponding to every data point in line A.

Thus, converter 316 uses data collected over a larger interval of fan beam projections than prior art converters (i.e., the interval ($-2\gamma_m$, $2\pi+2\gamma_m$), rather than the smaller interval (0, $2\pi$)). However, converter 316 generates parallel beam projections, as illustrated in FIG. 14C, that do not include any more data points than parallel beam projections generated by prior art converters, as illustrated in FIG. 8C. This is so because converter 316 discards some of the data points collected by the detector system when forming the parallel beam projections. The discarded data points are illustrated in FIG. 14A by the dashed lines 350. Specifically, the data discarded is that data collected by detector A between $2\pi-2\gamma_m$ and $2\pi+2\gamma_m$; detector B between $-2\gamma_m$ and $+2\gamma_m$; and detector C between $-2\gamma_m$ and 0 and between $2\pi$ and $2\pi+2\gamma_m$. Each detector therefore is used to process fan beam projection data through $2\pi+4\gamma_m$, but uses only $2\pi$ worth of data for generating the parallel beam projection data.

As those skilled in the art will appreciate, in alternate embodiments, scanner 300 may use extrapolation rather than interpolation to generate some of the estimated CZA data points. In these embodiments, scanner 300 may generate a tomogram at a slice plane of $\pi$ from fan beam projection data collected for fan beam projection angles in the interval (0, $2\pi$). However, since interpolation is generally more accurate and reliable than extrapolation, parallel beam converter 316 preferably uses the extra $4\gamma_m$ of fan beam projection data.

Figure 15A:
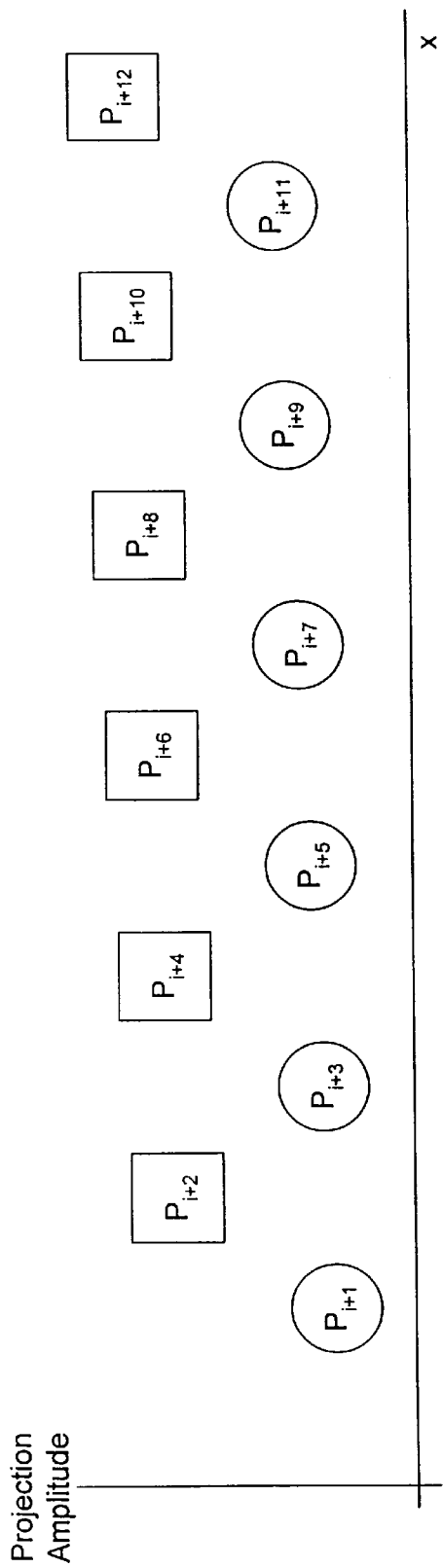
FIG. 15A shows a simplified graph of some data points in a parallel beam projection generated during a CSH scan.
Figure 15B:
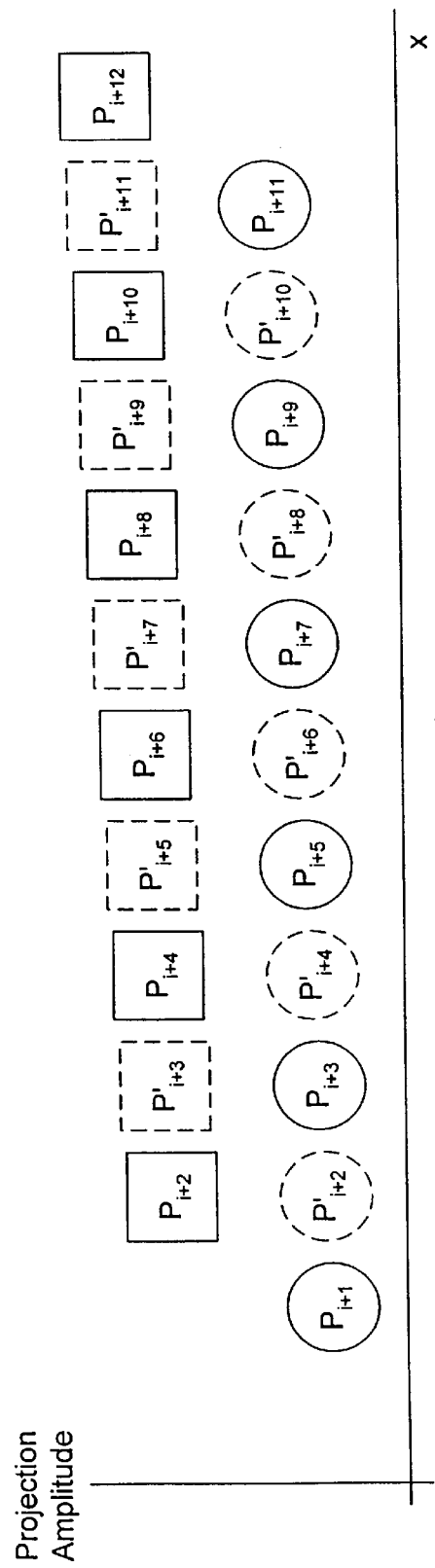
FIG. 15B illustrates in simplified graphical form the results of a first interpolation operation performed according to one aspect of the invention for generating data points in an interpolated CZA projection from the data points shown in FIG. 15A.
Figure 15C:
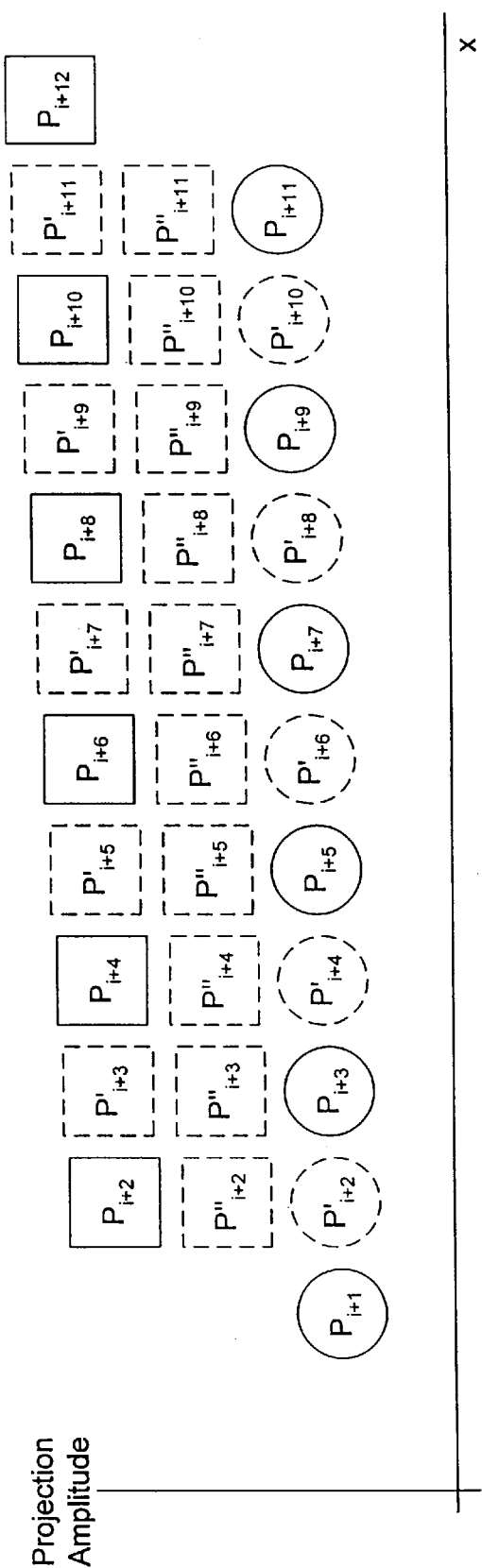
FIG. 15C illustrates in simplified graphical from the results of a second interpolation operation performed according to one aspect of the invention for generating data points in an interpolated CZA projection from the data points shown in FIG. 15B.

FIGS. 15A, 15B, and 15C illustrate the operation of improved interpolation system 318. FIG. 15A shows a graph of a portion of a parallel beam projection generated by parallel beam converter 316. Symmetric detector system 310 is assumed to include N individual detectors, so every parallel beam projection generated by parallel beam converter 316 will include 2N data points $P_k$ for all integers k from one to 2N. FIG. 15A illustrates only the points $P_k$ for all integers k from i+1 to i+12. In FIG. 15A, the odd data points are represented as circles, and the even data points are represented as squares. As stated above, there tends to be an amplitude offset between the even and odd data points because they are generated at substantially different Z-axis locations.

Interpolation system 318 performs two distinct interpolation operations on the data in every parallel beam projection to generate the interpolated parallel beam projections. FIG. 15B illustrates the results of the first of these interpolation operations. In this operation, interpolation system 318 uses the odd data points to generate an even interpolated data point between every pair of adjacent odd data points in each parallel beam projection. In this operation, interpolation system 318 also uses the even data points to generate an odd interpolated data point between every pair of adjacent even data points in each parallel beam projection. More specifically, during the first interpolation operation, interpolation system 318 generates an interpolated data point $P'_k$ having an X-axis coordinate lying between the X-axis coordinates of the original data points $P_{k-1}$ and $P_{k+1}$, for all integers k from one to 2N−1. For example, during the first interpolation operation, interpolation system 318 generates the interpolated even data point $P'_{i+2}$ between the odd data points $P_{i+1}$ and $P_{i+3}$, and also generates the interpolated odd data point $P'_{i+3}$ between the even data points $P_{i+2}$ and $P_{i+4}$. In FIG. 15B, the interpolated even data points are represented as dashed circles, and the interpolated odd data points are represented as dashed squares.

As shown in FIG. 15B, every interpolated data point $P'_k$ shares the same X-axis coordinate as an original data point $P_k$ for all integers k from one to 2N. The interpolated data point $P'_k$ essentially represents an estimate of a data point that would have been generated in response to a fictitious ray that was antiparallel and coincident with the ray used to generate the original data point $P_k$, if a fictitious detector were present in the detector system to measure this fictitious ray. Since detector system 310 is characterized by a quarter detector offset, no detectors are physically present in the detector system 310 to measure these fictitious rays. However, interpolation system 318 uses the data collected by the quarter detector offset system 310 to estimate the data points that would have been generated by such fictitious detectors. In this manner, interpolation system 318 preserves the high resolution potential of the data collected by the quarter detector offset system 310. Without applying weighting factors to the original data points as has been done by prior art methods, interpolation system 318 does not have to filter out the large amplitude differences induced by the weighting factors between adjacent data points. Consequently, the present invention of using interpolation system 318 achieves higher spatial resolution than the prior art methods.

FIG. 15C illustrates the results of the second interpolation operation performed by system 318. The Z-axis coordinate of the interpolated point $P'_k$ lies between the Z-axis coordinates of the original data points $P_{k-1}$ and $P_{k+1}$. For every pair of interpolated and non-interpolated data points $P'_k$ and $P_k$, respectively, one of the points lies on one side of a slice plane, and the other point lies on the other side of the slice plane. In the second interpolation operation, interpolation system 318 generates a twice interpolated data point $P''_k$ according to a weighted average of the pair of interpolated and non-interpolated data points $P'_k$ and $P_k$, respectively, for all integers k from one to 2N. Interpolation system 318 selects the coefficients for the second interpolation operation so that the Z-axis coordinates of all the twice interpolated data points $P''_k$ are all equal to $z_{sp}$. Therefore, the collection of all the twice interpolated data points $P''_k$, for all k from one to 2N, represents an interpolated CZA parallel beam projection at the slice plane. Interpolation system 318 generates an interpolated CZA parallel beam projection corresponding to each of the parallel beam projections generated by parallel beam converter 316 so that all of the interpolated CZA parallel beam projections share the same slice plane. Back projector 320 then generates a tomogram from these interpolated CZA parallel beam projections.

The above-described mode of operation for interpolation system 318 is advantageous because it provides for generation of tomograms of improved quality. Further, this mode is advantageous because it is relatively straight forward and simple to understand. However, as will be discussed in greater detail below, this mode requires more computations than are necessary and is therefore a non-preferred mode of operation. The preferred mode of operation of interpolation system 318 will now be discussed in connection with FIGS. 15D and 15E.

Figure 15D:
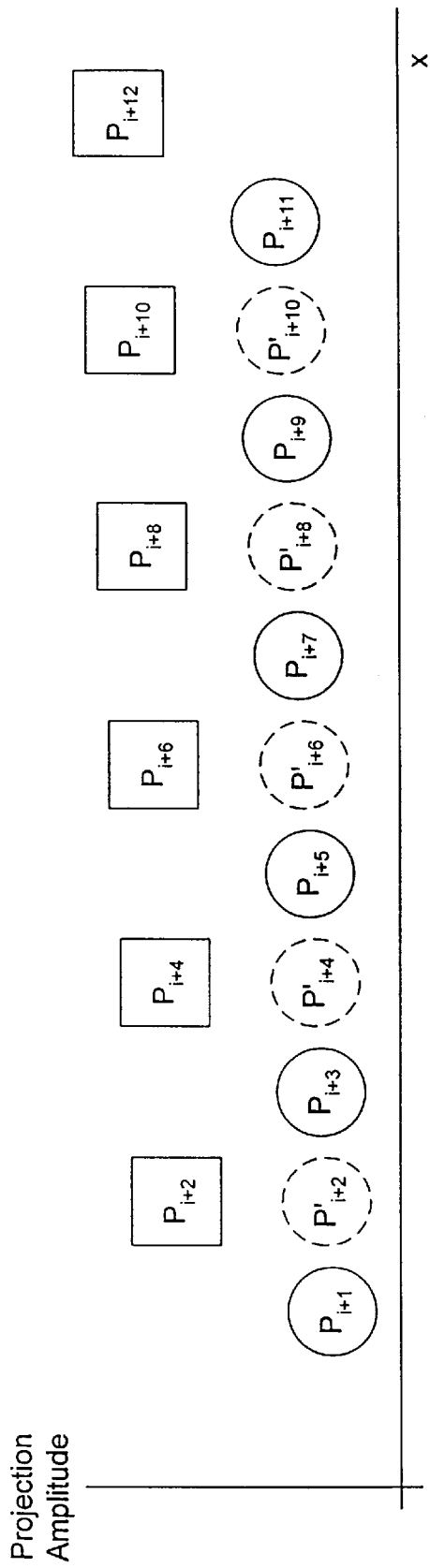
FIG. 15D illustrates in simplified form the results of a preferred first interpolation operation performed according to one aspect of the invention for generating data points in an interpolated CZA projection from the data points shown in FIG. 15A.

In the preferred mode of operation, interpolation system 318 still performs two distinct interpolation operations. The preferred first interpolation operation is nearly identical to the interpolation operation that was discussed above in connection with FIG. 15B. However, as is illustrated in FIG. 15D, in the preferred first interpolation operation, interpolation system 318 only generates interpolated even data points and does not generate any interpolated odd points. More specifically, in the preferred first interpolation operation, interpolation system 318 generates an interpolated even data point $P'_{2k}$ between the data points $P_{2k-1}$ and $P_{2k+1}$ for all k from one to N. As was the case in the non-preferred operation, the interpolated data point $P'_{2k}$ is generated so that its X-axis coordinate is equal to the X-axis coordinate of the original data point $P_{2k}$.

Figure 15E:
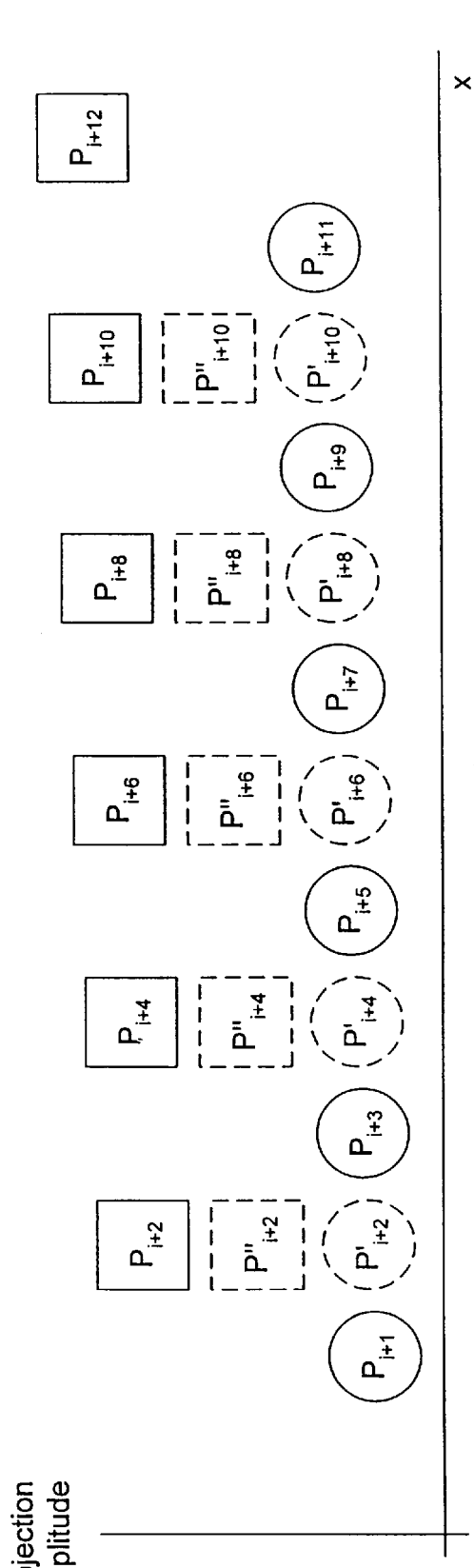
FIG. 15E illustrates in simplified form the results of a preferred second interpolation operation performed according to one aspect of the invention for generating data points in an interpolated CZA projection from the data points shown in FIG. 15D.

The preferred second interpolation operation is nearly identical to the operation illustrated in FIG. 15C. However, as is illustrated in FIG. 15E, in the preferred second interpolation operation, interpolation system 318 only generates even twice interpolated points and does not generate any odd twice interpolated points. More specifically, in the preferred second interpolation operation, interpolation system 318 generates an even twice interpolated point $P''_{2k}$ according to a weighted average of the even non-interpolated and interpolated data points $P_{2k}$ and $P'_{2k}$, respectively, for all k from one to N. In the preferred second interpolation operation, the coefficients for the interpolation are selected so that if the Z-axis coordinate of the midpoint between data points $P_{2k-1}$ and $P_{2k+1}$ is equal to $z_{sp}+\delta$ (where $z_{sp}$ is the Z-axis coordinate of the slice plane), then the Z-axis coordinate of the twice interpolated data point $P''_{2k}$ is equal to $z_{sp}-\delta$.

Following the second preferred interpolation operation, interpolation system 318 applies the collection of all the original odd data points and all the twice interpolated even data points to back projector 320 as an interpolated CZA projection. All of these data points do not share the same Z-axis coordinate. However, this mode of operation takes advantage of the convolution associated with filtered backprojection performed by back projector 320. As is well known, this convolution provides local averaging. Since all the adjacent data points $P_k$ and $P''_{k+1}$ in the interpolated CZA projections are equally spaced on opposite sides of the slice plane, back projector 320 essentially averages these data points to generate data points at the slice plane.

The preferred mode of operation for interpolation system 318 which has been discussed in connection with FIGS. 15D and 15E is preferred over the mode illustrated by FIGS. 15B and 15C because the preferred mode achieves superior results with fewer computations. More specifically, the preferred mode of operation requires half as many computations as are required by the non-preferred mode. Also, when interpolation system 318 operates according to the non-preferred mode, every data point in the CZA projections is the result of an interpolation calculation, whereas in the preferred mode of operation, only half the data points in the CZA projections are the result of an interpolation calculation. The other half of the data points are original, and therefore higher fidelity, data points. More importantly, the Z-axis coordinate of this half of the original data points, such as data points on line A, B, and C in FIG. 14B over the rotation angle interval ($\pi/2-2\gamma_m$, $3\pi/2+2\gamma_m$), is closer to the slice plane. They carry more weight to the interpolated CZA projections for reconstructing the slice plane. Therefore, the preferred mode produces higher fidelity tomograms.

In both non-preferred and preferred modes of operation, interpolation system 318 may use at least two different techniques of performing the first interpolation operation. The first technique is referred to as a Fourier technique, and the second technique is referred to as spatial domain processing.

With reference to FIG. 15D, in the first interpolation operation, interpolation system 318 uses the odd data points to generate an interpolated even data point $P'_{2k}$ between the data points $P_{2k-1}$ and $P_{2k+1}$ for all k from one to N. In the Fourier technique, the interpolated data points $P'_{2k}$ are computed by first generating a forward Fourier transform $F(f)$ of the odd data points $P_{2k+1}$ for all k from zero to N−1. $F(f)$ is defined over a frequency range $(0, f_{max})$. Then a second Fourier transform function $F'(f)$ is generated so that $F'(f)=F(f)$ for f in the range $(0, f_{max})$ and so that $F'(f)=0$ for f in the range $(f_{max}, 2f_{max})$. By design, $F'(f)$ has exactly the same spectral content as $F(f)$, however $F'(f)$ is defined over a frequency range that is twice as large as the range of $F(f)$. The inverse Fourier transform of $F'(f)$ is then calculated, and this inverse transform function will include all the original data points $P_{2k+1}$, as well as all the desired interpolated data points $P'_{2k}$, for all k from zero to N−1. This type of Fourier technique is a well known method of interpolation and it is advantageous because the spectral content of the resultant data is equivalent to the spectral content of the original data. However, this method is disadvantageous because it is relatively computationally intensive.

The spatial domain processing technique may be implemented as linear or higher order interpolations. One preferred spatial domain processing technique for use with the invention is a fourth-order Lagrange interpolation, although other Lagrange interpolations can be used such as a sixth-order Lagrange interpolation. The fourth-order interpolation generates satisfactory results and is relatively computationally simple. In this form of interpolation neighboring data point values on each side of the interpolated data point are used to determine the value of the interpolation. One preferred form of spatial domain processing for use in the first interpolation operation is described by the following Equation (1), although those skilled in the art will appreciate that other forms of interpolation the number of neighboring data point values as well as the weighting coefficient values used with each neighboring value could of course be used.

$$P'_k = 0.53125 * (P_{k-1} + P_{k+1}) - 0.03125 * (P_{k-2} + P_{k+2}) \quad (1)$$

As stated above, in the non-preferred mode of operation for interpolation system 318, the second interpolation operation (see FIG. 15C) generates the twice interpolated data points $P''_k$ for all k from one to 2N so that they all share the same Z-axis coordinate $z_{sp}$. The twice interpolated data points $P''_k$ may be calculated according to the following Equation (2).

$$P''_k = P'_k + \frac{(P_k - P'_k)\left(\frac{\phi}{2\pi} + \frac{m}{\text{MAX}}\right)}{\left(0.5 + \frac{2m}{\text{MAX}}\right)} \text{ for even } k \quad (2)$$

$$P''_k = P_k + \frac{(P'_k - P_k)\left(\frac{\phi}{2\pi} + \frac{m}{\text{MAX}}\right)}{\left(0.5 + \frac{2m}{\text{MAX}}\right)} \text{ for odd } k$$

In the above Equation (2), the variable "$\phi$" represents the parallel beam projection angle for the interpolated CZA parallel beam projection to which the data point $P''_k$ belongs, and the variable "m" represents the equivalent number of detectors between the data point $P_k$ and the data point at the center of the parallel beam projection. If k is ranged from 1 to 2N, then $$m = (k-N)/2 - 0.25 \quad (3)$$

where the factor 0.25 accounts for the quarter detector offset. The variable MAX represents the number of detectors that would make the fan angle $2\pi$ (i.e., the angle $2\gamma_m$ of a symmetric detector array in FIG. 11 becomes a full circle). For example, in the Anatom scanner, the angle subtended by each detector is 0.125°, MAX is equal to 2880 (i.e., 360/0.125). In Equation (2), the ratio m/MAX is derived from $\gamma/2\pi$, where $\gamma$ is the angle indicated in FIG. 11 of the detector which generates the data point $P_k$.

In the preferred mode of operation of interpolation system 318 (see FIGS. 15D and 15E), the even interpolated data points $P'_k$ are preferably generated according to the above-Equation (1). As was stated above, the coefficients for the second interpolation operation are selected so that if the Z-axis coordinate of the data point $P_{2k-1}$ is equal to $z_{sp}+\delta$ (where $z_{sp}$ is the Z-axis coordinate of the slice plane), then the Z-axis coordinate of the twice interpolated data point $P''_{2k}$ is equal to $z_{sp}-\delta$. The twice interpolated even data points, for example, may be generated according to the following Equation (4).

$$P''_k = P'_k + \frac{(P_k - P'_k)C_1(\phi, m)}{C_2(m)} \text{ for } \phi > 0 \quad (4)$$

$$P''_k = P'_k + \frac{(P_k - P'_k)(-C_1(\phi, m))}{C_3(m)} \text{ for } \phi < 0$$

where $$C_1(\phi, m) = \left(\frac{\phi}{\pi} + \frac{2m}{\text{MAX}}\right)$$

$$C_2(m) = \left(0.5 + \frac{2m}{\text{MAX}}\right)$$

$$C_3(m) = \left(0.5 - \frac{2m}{\text{MAX}}\right)$$

As shown by the above Equation (4), the value of the data point $P''_k$ depends on the values of the three functions $C_1$, $C_2$, and $C_3$. $C_2$ and $C_3$ are functions of the single variable "m". So the functions $C_2$ and $C_3$ may of course be precalculated for all values of "m" and stored in a look-up-table (LUT). $C_1$ is a function of two variables, $\phi$ and m. $C_1(\phi,m)$ may be rewritten as a function of the variables q and m according to the following Equation (5).

$$C_1(q, m) = \frac{q}{V} + \frac{2m}{\text{MAX}} \quad (5)$$

where the variable "q" represents the projection number and the constant V represents the total number of parallel beam projections used. In the above-mentioned Anatom scanner, the total number of fan beam projections is equal to MAX, and a decimation factor of three is applied (i.e., three projections are properly combined or averaged to generate a single decimated projection). So in the Anatom, V is equal to MAX/6 for the interleaved parallel beam projections, and the function $C_1(q,m)$ reduces to the following Equation (6).

$$C_1(q, m) = \frac{2(3q + m)}{\text{MAX}} \quad (6)$$

From Equation (6) it is apparent that $C_1(q+1,m)$ is equal to $C_1(q,m+3)$. So the coefficients $C_1$ for a particular view (e.g., view number q+1) may be generated by shifting the coefficients used for the previous view (i.e., view number q) by three points. So the coefficients $C_1(q,m)$ may all be precalculated and stored in a LUT, and the coefficients may be generated for any particular view number q by using an appropriate address offset to access the LUT. This has the advantage of eliminating the need for a 2D LUT, and using a 1D LUT with extended detector numbers used in accordance with Equation 6. Sequential values from this lookup table will be used as the first scaling factor for a particular projection or view angle. The starting address of the 1D LUT for these sequential values will be shifted from successive projection angles.

Figure 16:
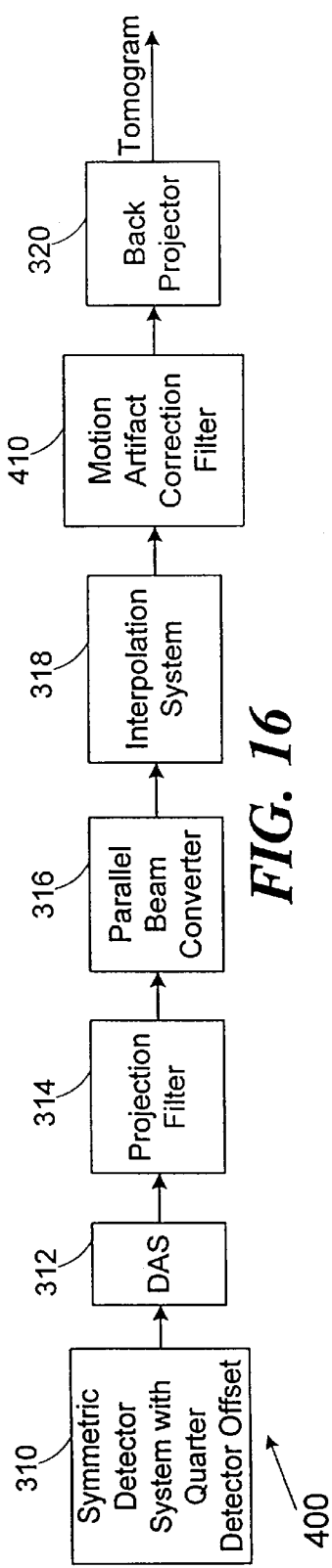
FIG. 16 shows a block diagram of a portion of another CT scanner constructed according to one aspect of the invention.

FIG. 16 shows a block diagram of another embodiment of a CT scanner 400 constructed according to the invention. Scanner 400 is similar to scanner 300 (shown in FIG. 13), however, scanner 400 additionally includes a motion artifact suppression filter 410 disposed between the interpolation system 318 and the back projector 320. Motion artifact suppression filter 410 preferably is similar to the filter described in U.S. Pat. No. 5,671,263 entitled MOTION ARTIFACT SUPPRESSION FILTER FOR USE IN COMPUTED TOMOGRAPHY SCANNER, which is assigned to the assignee of the present invention and which is hereby incorporated by reference.

Motion artifact suppression filter 410 suppresses artifacts in the tomograms generated by scanner 400 that are caused by certain motions of the patient during a helical scan. During a helical scan, the patient and disk are translated relative to one another along the Z-axis while the disk is rotated about the patient. The interpolation system 318 provides compensation for this predictable, well defined, relative axial motion of the patient in the direction of the Z-axis. However, in addition to this controlled axial motion, the patient might make other movements during a scan. These "other movements" might for example be related to breathing, or heart beats, or involuntary twitches. For convenience of exposition, these "other movements" shall be referred to herein as "non-axial movements". Interpolation system 318 does not provide compensation for non-axial movements, and these movements can introduce artifacts, that appear more or less as curving streaks, into the tomograms. Motion artifact suppression filter 410 provides compensation for these types of non-axial movement induced artifacts so as to reduce the motion artifacts in the tomograms generated by scanner 400.

In addition, the motion artifact suppression filter can enhance the interpolation system 318. If some of the projection amplitudes vary greatly as the result of axial movement across the slice plane, the interpolated CZA data may contain residual motion errors which can introduce artifact to the tomogram. Also, in the preferred mode of operation of interpolation system 318, the even data points are twice interpolated to Z-axis coordinate at $z_{sp}-\delta$ while the odd data points remain at $z_{sp}+\delta$. Slight discrepancy in projection amplitude is expected between adjacent even and odd points of the interpolated CZA data, due to their Z-axis coordinate difference of $2\delta$. The motion artifact suppression filter 410 can correct these residual axial movement artifact well, and thus relieve convolution filter from performing such corrections. Consequently, high-pass filters can be used for the convolution in the filtered backprojection to achieve higher image resolution.

Figure 17:
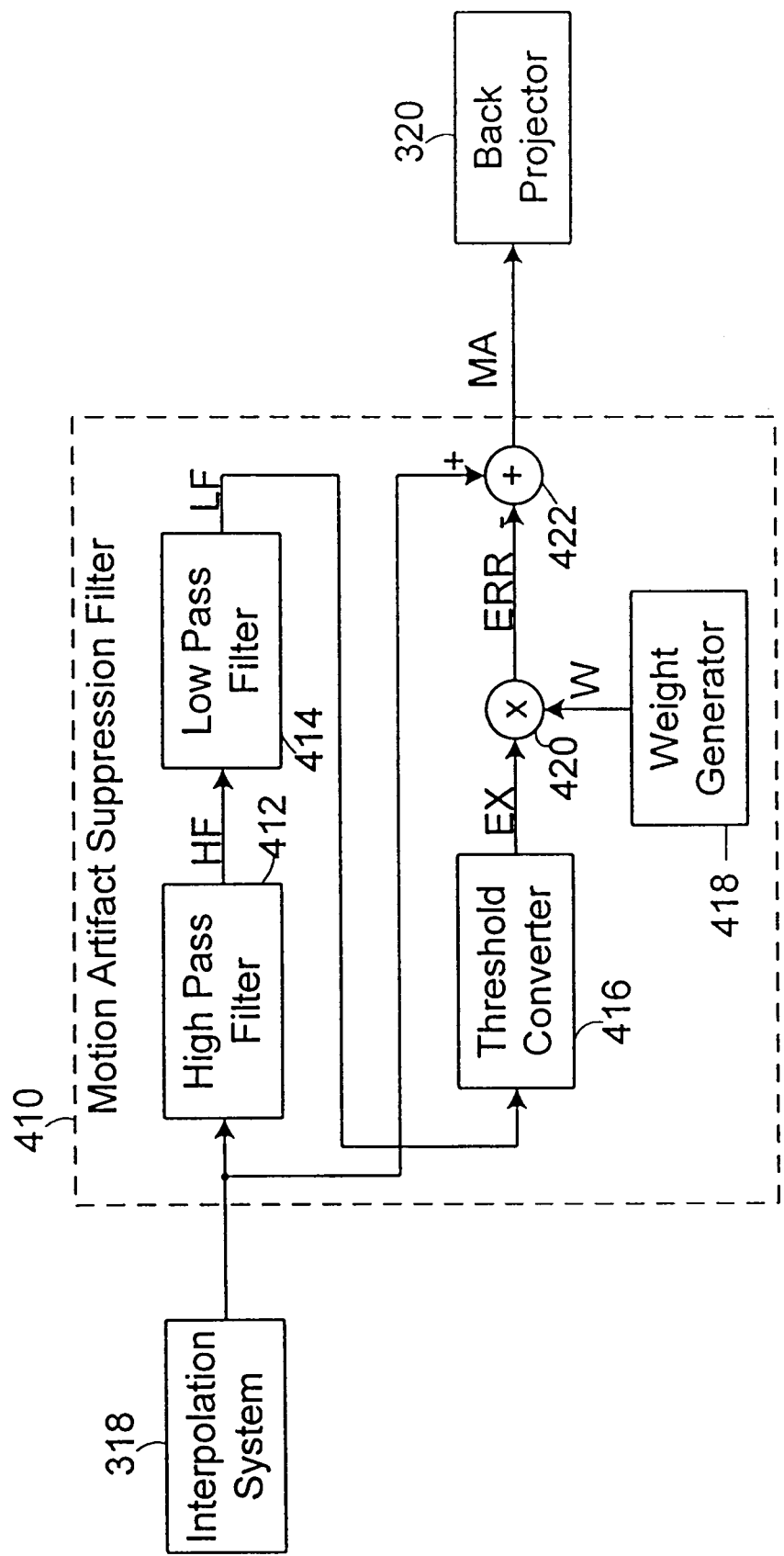
FIG. 17 shows a block diagram of the preferred motion artifact suppression filter shown in FIG. 16.

FIG. 17 shows a block diagram of a preferred motion artifact suppression filter 410, which includes a high pass filter 412, a low pass filter 414, a threshold converter 416, a weight generator 418, a two input terminal multiplier 420, and a two input terminal subtractor 422. The interpolated CZA parallel beam projections generated by interpolation system 318 are applied to the high pass filter 412 and to a positive input terminal of subtractor 422. The high pass filter 412 generates high frequency data points that are applied to low pass filter 414. The latter generates low frequency data points that are applied to threshold converter 416. Converter 416 generates excess data points that are applied to one input terminal of multiplier 420. Weight generator 418 generates a weight that is applied to the other input terminal of multiplier 420. The latter generates error data points that are applied to the negative input terminal of subtractor 422. Finally, subtractor 422 generates motion artifact corrected projections that are applied to back projector 320. As will be discussed in greater detail below, by using the motion artifact corrected projections generated by motion artifact suppression filter 410, rather than the interpolated CZA parallel beam projections generated by interpolation system 320, back projector generates improved tomograms that are characterized by fewer artifacts.

The interpolated CZA parallel beam projections generated by interpolation system 318 may be represented as a set of data points $CZA_k$ for all k from one to 2N. In accordance with the discussion above of interpolation system 318, the data points $CZA_k$ may be equal to twice interpolated data points $P''_k$ or to original data points $P_k$, depending on the mode of operation of the interpolation system 318 and the value of the index k.

High frequency filter 412 receives the data points $CZA_k$ for all k from one to 2N and generates therefrom a set of high frequency data points $HF_k$ for all k from one to 2N. High frequency filter 412 preferably generates each data point $HF_k$ so that it represents the amplitude difference between the adjacent data points $CZA_{k-1}$, $CZA_k$, and $CZA_{k+1}$. As stated above, since the even and odd data points in a parallel beam projection are generated at different times and at different Z-axis coordinates, there tends to be an amplitude offset between the even and odd data points. High frequency filter 412 generates the data points $HF_k$ so that they are representative of this amplitude offset. In general, relatively small values of the data point $HF_k$ are indicative of an amplitude offset caused by a varying density profile of the patient. However, relatively large values of the data point $HF_j$ are generally indicative of non-axial movements and residual axial movements. In one preferred embodiment, the high frequency filter 412 generates the high frequency data points according to the following Equation (7).

$$HF_k = CZA_k - \frac{CZA_{k-1} + CZA_{k+1}}{2} \quad (7)$$

The low frequency filter 414 receives the high frequency data points $HF_k$ and generates therefrom the low frequency data points $LF_k$ for all k from one to 2N. In alternative embodiments, low frequency filter 414 may be eliminated from motion artifact suppression filter 410. However, while not required, the low frequency filter 414 improves the performance of motion artifact filter 410. Low frequency filter 414 generates each data point $LF_k$ so that it represents a weighted average of neighboring high frequency data points $HF_k$. In one preferred embodiment, low frequency filter 414 generates the low frequency data points $LF_k$ according to the following Equation (8). In one preferred embodiment, the coefficients $A_0$, $A_1$, and $A_2$ used in Equation (8) are equal to 0.3, −0.25, and 0.1, respectively. Because the sign of $HF_k$ alternates between even and odd number points, $A_1$ is chosen negative to make all three products in Equation (8) in the same sign.

$$LF_k = A_0 * HF_k + A_1 * (HF_{k-1} + HF_{k+1}) + A_2 * (HF_{k-2} + HF_{k+2}) \quad (8)$$

The low frequency data points $LF_k$ are applied to the threshold converter 416 which generates therefrom the excess data points $EX_k$ for all k from one to 2N. In one preferred embodiment, threshold converter 416 generates the excess data points $EX_k$ according to the following Equation (9).

$$EX_k = \begin{cases} LF_k - THR, \text{ for } LF_k > THR \\ LF_k + THR, \text{ for } LF_k < -THR \\ 0, \text{ otherwise} \end{cases} \quad (9)$$

In Equation (9), the variable THR is a threshold of positive value. When the absolute value of the data point $LF_k$ is greater than the threshold THR, the data point $LF_k$ is considered to be representative of non-axial motion and the residual axial motion, and the corresponding excess data point $EX_k$ is set equal to the amount by which the data point $LF_k$ exceeded the threshold. When the absolute value of the data point $LF_k$ is less than the threshold THR, then any non-zero value of $LF_k$ is taken to be representative of a varying density profile of the patient, and the corresponding data point $EX_k$ is set equal to zero. In one preferred embodiment of filter 410, the value of the threshold THR is set equal to 0.01. However, other values of the threshold could of course be used. The value of the threshold is preferably set so that it discriminates well between motion (non-axial or residual axial) and varying density profiles inherent in typical patients.

The weight generator 410 generates a weight equal to one half. The primary difference between motion artifact suppression filter 410 and the filter described in the above-referenced U.S. Pat. No. 5,671,263 relates to the function of the weight generator. In the filter described in that patent, rather than generate a single weight of one half, the weight generator generates a set of weights. The majority of the weights generated by that weight generator are one half, however, the weights near the starting and finishing angles and near an intermediate angle tapered towards either one or zero. As is fully described in that patent, tapering the weights in this fashion provides compensation for differences in projections collected near the starting and finishing angles (e.g., projections at fan beam projection angles of zero and 360 degrees). Tapering the weights in filter 410 is unnecessary since interpolation system 318 already provides compensation for differences in projections collected near the starting and finishing angles.

Multiplier 420 multiplies the excess data points $EX_k$ by the weight of one half to generate the error data points $ERR_k$, such that even and odd data points share equal weight in the correction for the motion error. Other weight values would also work as long as the sum of the weights for the even and odd data points is one. In other embodiments of filter 410, weight generator 418 and multiplier 420 are eliminated and their functions are performed by threshold converter 416. However, these components have been included to facilitate understanding the relationship between filter 410 and the filter described in the above-referenced U.S. Pat. No. 5,671, 263.

Subtractor 422 receives the error data points $ERR_k$ and the interpolated parallel beam projection data points $CZA_k$ and generates therefrom the motion artifact corrected projections. Each motion artifact corrected projection may be represented as a set of data points $MA_k$ for all k from one to 2N. Subtractor 422 generates each data point $MA_k$ by subtracting the error data point $ERR_k$ from the corresponding parallel beam data point $CZA_k$.

In operation, motion artifact suppression filter 410 tends to reduce the amplitude offset between even and odd data points in the motion artifact corrected projections. However, since motion artifact suppression filter 410 only alters the values of the data points when the low frequency data points exceed the threshold THR, the operation of filter 410 is inherently non-linear. The non-linear nature of filter 410 allows the filter to discriminate between amplitude offsets between even and odd data points that are representative of motions and offsets that are due to other causes. Filter 410 operates to reduce only the amplitude offsets that are caused by non-axial motions and residual axial motions and thereby reduces the motion induced artifacts in the tomograms generated by scanner 400.

Figure 18:
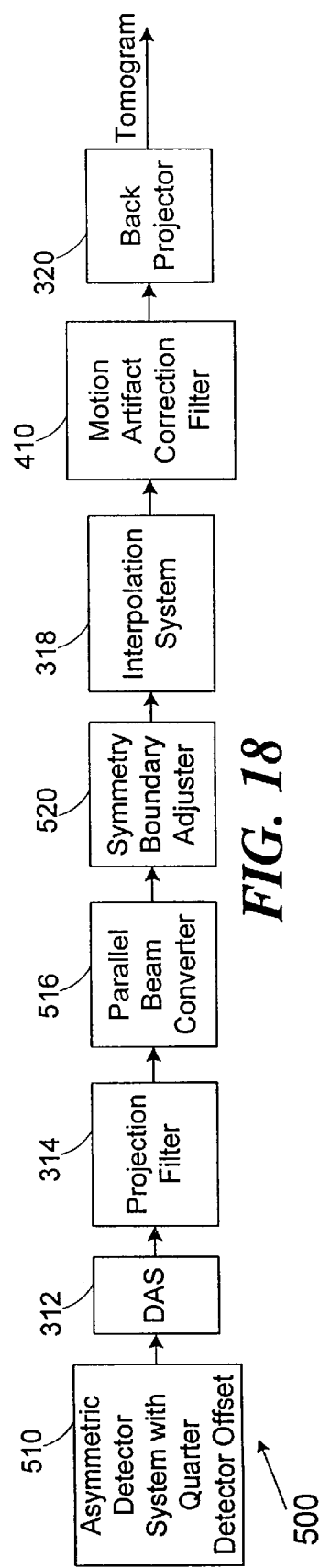
FIG. 18 shows a block diagram of a portion of a preferred CT scanner constructed according to one aspect of the invention.

Scanners 300 and 400 which have been discussed above are useful in connection with symmetric detector systems. The invention however also provides methods and apparatus for generating tomograms from helical scan data collected with an asymmetric detector system. FIG. 18 shows a block diagram of one preferred embodiment of a portion of a scanner 500 constructed according to the invention. Scanner 500 is similar to scanner 400 (shown in FIG. 14), however, scanner 500 includes an asymmetric offset detector system 510 rather than a symmetric offset detector system 310. Scanner 500 also includes a parallel beam converter 516 (rather than converter 316) which has been adapted for use with asymmetric offset detector system 510. Scanner 500 also includes a symmetry boundary adjuster 520 disposed between parallel beam converter 516 and interpolation system 318. Symmetry boundary adjuster 520 receives the parallel beam projections generated by converter 516 and generates therefrom adjusted projections and applies these adjusted projections to interpolation system 318. As stated above and shown in FIG. 12, one problem with prior art methods of helical scanning is that they can not adequately process the non-interleaved exterior portions of parallel beam projections generated by the asymmetric portion 14b in FIG. 11. Scanner 500 overcomes this limitation of the prior art.

As will be discussed in greater detail below, scanner 500 uses fan beam projection data collected for helical projection angles in the interval $(x-2\pi, x+2\pi)$ to generate a tomogram at a slice plane along the Z-axis corresponding to the helical projection angle of x. So referring to FIG. 3B, scanner 500, for example, may generate a tomogram at a slice plane corresponding to a helical projection angle of $4\pi$ from fan beam projection data collected for helical projection angles in the range $(2\pi, 6\pi)$. Since the disk rotates $4\pi$ radians (or 720°) to collect enough data for scanner 500 to generate a single tomogram, the patient and disk are translated relative to one another along the Z-axis by a distance 2h while this data is collected. However, the effective slice plane width for tomograms generated by scanner 500 is not equal to 2h. Rather, each tomogram generated by scanner 500 has two associated slice plane widths, a first slice plane width associated with data collected by the symmetric portion of the detector system 510 and a second slice plane width associated with data collected by the asymmetric portion of the detector system 510. The first slice plane width is associated with a translation distance of h and the second slice plane width is associated with a translation distance of 2h.

Figure 11:
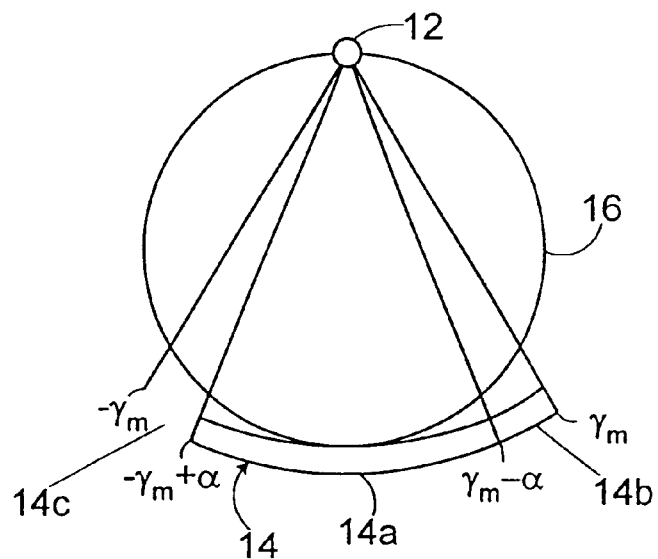
FIG. 11 shows a simplified axial view of a prior art CT scanner with an asymmetric detector system.
Figure 4A:
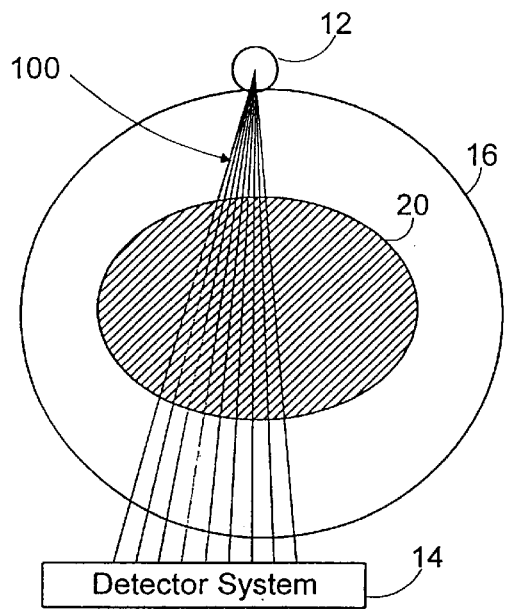
FIG. 4A illustrates in a simplified schematic drawing some of the rays of a fan beam projection.
Figure 4B:
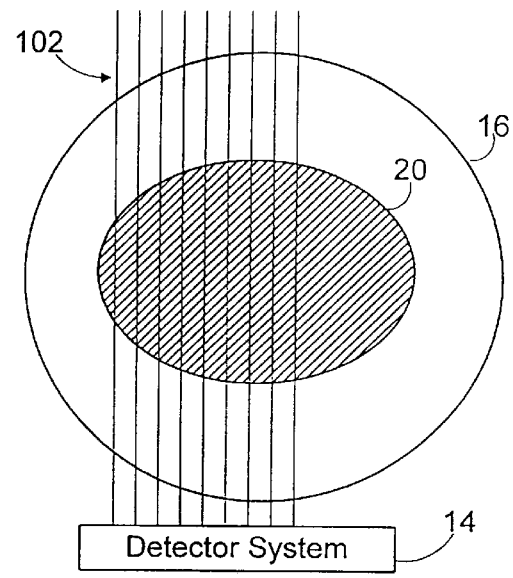
FIG. 4B illustrates in a simplified schematic drawing some of the rays of a parallel beam projection.
Figure 5A:
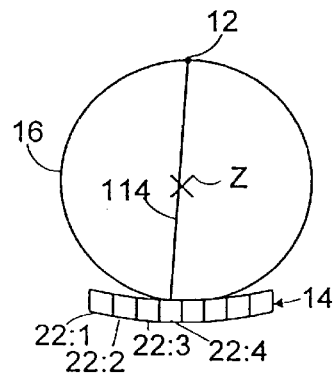
FIGS. 5A and 5B illustrate in a simplified schematic drawing a method of generating reordered projections from fan beam projections.
Figure 5B:
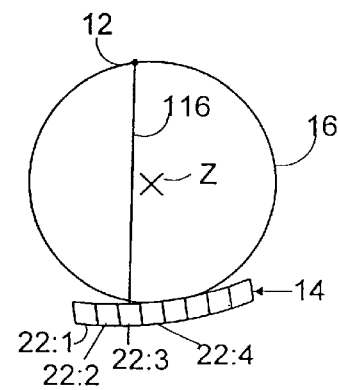
Figure 12:
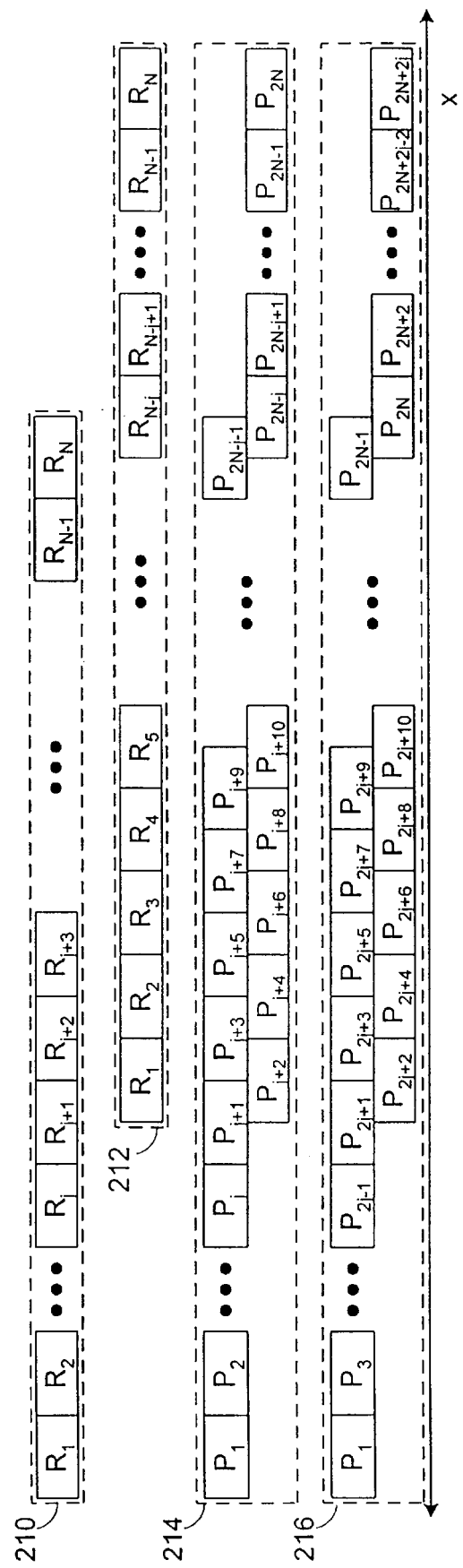
FIG. 12 illustrates in simplified form, the spatial relationship of the X-axis coordinates of two reordered projections generated at reordered projection angles of 0° and 180°, and also illustrates the X-axis coordinates of a parallel beam projection generated from those two reordered projections.

Asymmetric offset detector system 510 is of the type shown in FIG. 11 and extends from a detector angle of $-\gamma_m+\alpha$ to $\gamma_m$. Further, detector system 510 may be thought of as including a symmetric portion 14a and an asymmetric portion 14b, as well as having a missing portion 14c from what would otherwise be a symmetric arrangement. Detector system 510 may be considered as including N individual detectors, with asymmetric portion 14b including j detectors and symmetric portion 14a including N-j detectors.

Figure 19:
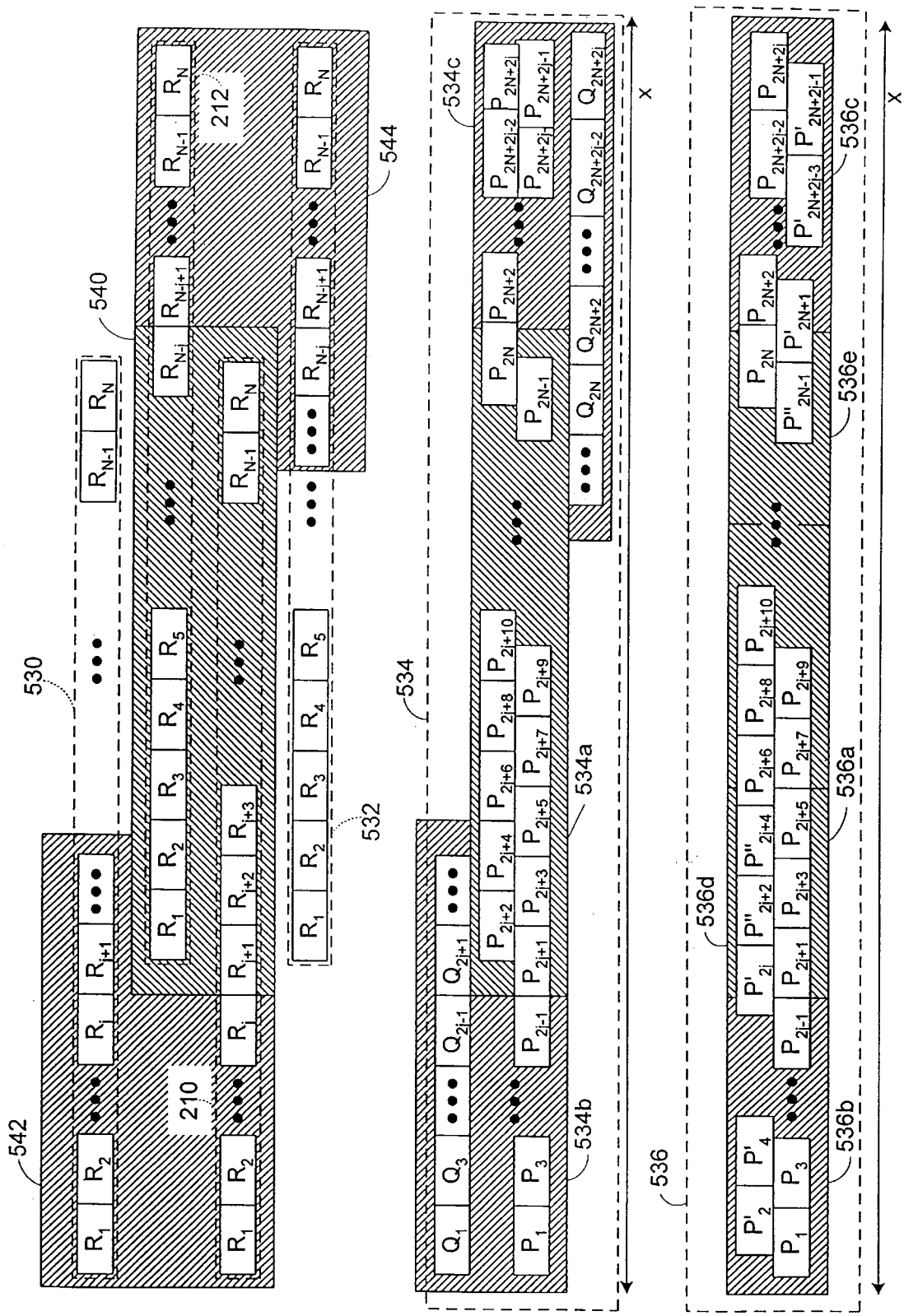
FIG. 19 is a spatial diagram illustrating the X-axis coordinates of the data points in four reordered projections generated at reordered projection angles of 0°, 180°, 360°, and 540°, and also illustrating the X-axis coordinates of the data points in a fully interleaved parallel beam projection generated according to the invention from those four reordered projections.

FIG. 19 illustrates the X-axis coordinates of four reordered projections 210, 212, 530, 532 generated from fan beam projections collected from asymmetric detector system 510. Reordered projections 210, 212, 530, 532 are generated according to the prior art methods discussed above for generating reordered projections from fan beam projections. FIG. 19 additionally illustrates the X-axis coordinates of a parallel beam projection 534 generated by parallel beam converter 516 and a fully interleaved parallel beam projection 536 generated by symmetry boundary adjuster 520.

In the illustration of a $4\pi$ radian rotation, reordered projections 530, 212, 210, and 532 are generated at reordered projection angles of $\beta$, $\beta+\pi$, $\beta+2\pi$, and $\beta+3\pi$, respectively. Improved parallel beam converter uses reordered projections 530, 212, 210, and 532 to generate the parallel beam projection 534. Parallel beam projection 534 includes a central region 534a, and two exterior regions 534b, 534c. The exterior regions 534b and 534c of projection 534 include the asymmetric portions of reordered projections 210, 212, and data points extracted from reordered projections 530 and 532. Symmetry boundary adjuster 520 uses these extracted data points to generate parallel beam projection 536. Unlike prior art parallel beam projections generated from data collected with an asymmetric detector system (such as projection 216 shown in FIG. 12), the parallel beam projection 536 is fully interleaved. The parallel beam projection 536 includes an interleaved central region 536a, two interleaved exterior regions 536b, 536c, and two interleaved boundary regions 536d, 536e. The number of extracted data points is M in each boundary region.

Improved converter 516 preferably uses the data in reordered projections 210, 212 collected by the symmetric portion 14a of the detector system 510 (i.e., the data enclosed within box 540) to generate the central portion 534a of projection 534. Converter 516 preferably uses the data in reordered projections 530 and 210 collected by the asymmetric portion 14b of the detector system 510 and M points in the symmetric portion of reordered projection 530 (i.e., the data enclosed within box 542) to generate the exterior region 534b of projection 534. Similarly, converter 516 preferably uses the data in reordered projections 212 and 532 collected by the asymmetric portion 14b of the detector system 510 and M points in the symmetric portion of 532 (i.e., the data enclosed within box 544) to generate the other exterior region 534c of projection 534.

More specifically, converter 516 uses the data points $R_k$ for all k from one to j in projection 210 to generate the odd data points $P_1$ to $P_{2j-1}$ in the exterior region 534b by setting the data point $P_{2k-1}$ equal to the data point $R_k$. Converter 516 uses the data points $R_k$ for all k from one to j+M in projection 530 to generate the extracted data points $Q_1$ to $Q_{2j+2M-1}$ in the exterior region 534b by setting the data point $Q_{2k-1}$ equal to the data point $R_k$. Converter 516 uses the data points $R_k$ for all k from N−j+1 to N in reordered projection 212 to generate the even data points $P_{2N+2}$ to $P_{2N+2j}$ in the exterior region 534c by setting the data point $P_{2k+2j}$ equal to data point $R_k$. Converter 516 uses the data points $R_k$ for all k from N−j−M+1 to N in reordered projection 532 to generate the extracted data points $Q_{2N-2M+2}$ to $Q_{2N+2j}$ in the exterior region 534c by setting the data point $Q_{2k+2j}$ equal to data point $R_k$. Converter 516 uses the data points $R_k$ for all k from j+1 to N in reordered projection 210 to generate the odd data points $P_{2j+1}$ to $P_{2N-1}$ in central region 534a by setting the data point $P_{2k-1}$ equal to the data point $R_k$. Converter 516 uses the data points $R_k$ for all k from 1 to N−j in reordered projection 212 to generate the even data points $P_{2j+2}$ to $P_{2N}$ in the central region 534a by setting the data point $P_{2k+2j}$ to the data point $R_k$.

Improved parallel beam converter 516 uses reordered projections separated by reordered projection angles of 180° to generate the central region 534a of projection 534. Converter 516 uses reordered projections separated by reordered projection angles of 360° to generate the exterior regions 534b, 534c of projection 534. This discrepancy between the angular separation between the reordered projections used to generate the central and exterior regions of every parallel beam projection causes tomograms generated by scanner 500 to have two associated slice plane widths as was discussed above.

Figure 20:
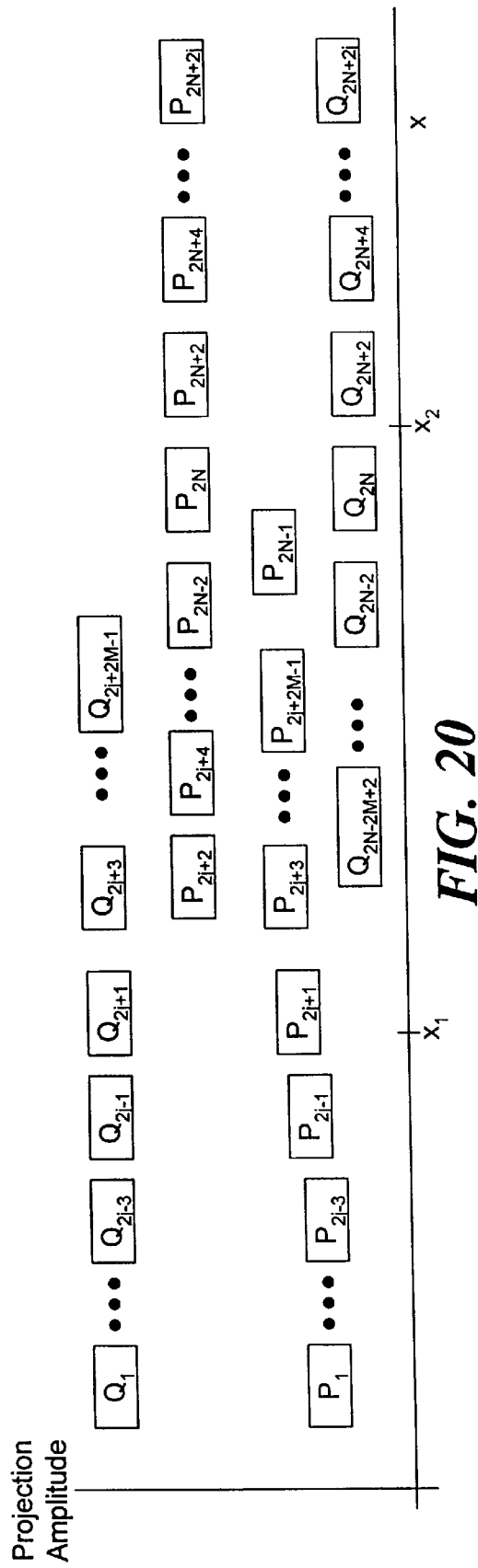
FIG. 20 shows a simplified graph of some of the data points including a parallel beam projection of interest generated at reordered projection angles of 180° and 360° and the data point extracted from reordered projection angles of 0° and 540° according to the invention.

FIG. 20 shows a graph of some of the data points in parallel beam projection 534. As illustrated, the change in amplitude between the odd data points $P_1$ to $P_{2N-1}$ tends to be gradual. Similarly, the change in amplitude between the extracted data points $Q_{2N-2M+2}$ to $Q_{2N+2j}$ tends to be gradual. However, there tends to be a relatively large amplitude offset, or discontinuity, between the adjacent data points $P_{2N-1}$ and $Q_{2N}$. Also, the change in amplitude between the extracted data points $Q_1$ to $Q_{2j+2M-1}$ tends to be rather gradual, and the change in amplitude between the even data points $P_{2j+2}$ to $P_{2N+2j}$ also tends to be rather gradual. However, there tends to be a relatively large amplitude offset, or discontinuity, between the adjacent data points $Q_{2j+1}$ and $P_{2j+2}$.

The tendency for there to be a discontinuity between the adjacent data points $P_{2N-1}$ and $Q_{2N}$ and between the adjacent data points $Q_{2j+1}$ and $P_{2j+2}$ may be understood by referring to FIG. 19. The adjacent data points $Q_{2j+1}$ and $P_{2j+2}$ are equal to the data points $R_{j+1}$ from reordered projection 530 and $R_1$ from reordered projection 212, respectively. Since these data points are from two different reordered projections generated 180° apart, there is a relatively large Z-axis offset between these data points, and this tends to result in an amplitude offset. Similarly, the adjacent data points $P_{2N-1}$ and $Q_{2N}$ are equal to the data point $R_N$ of the reordered projection 210 and $R_{N-j}$ of reordered projection 532. So there also tends to be a relatively large Z-axis offset, and a corresponding amplitude offset between these pairs of data points. These amplitude offsets, or discontinuities, may be thought of as occurring across a "symmetry boundary", since one of the data points in each pair is collected by a detector in the symmetric portion (at a detector angle of $-\gamma_m+\alpha$) and the other data point in each pair is collected by a detector in the asymmetric portion (at a detector angle slightly larger than $\gamma_m-\alpha$). If these extracted data points are used to fill the exterior regions without adjustment, these discontinuities occurring across the symmetry boundaries tend to create artifacts in the resulting tomograms.

Symmetry boundary adjuster 520 receives the parallel beam projections including extracted data points (such as projection 534 shown in FIG. 19) generated by parallel beam converter 516. Adjuster 520 generates an adjusted projection corresponding to every parallel beam projection received from converter 516. Adjuster 520 generates the adjusted projections so as to substantially remove, or suppress, the discontinuities across the above-discussed symmetry boundaries. Adjuster 520 preferably performs several distinct operations to remove these discontinuities.

Figure 21:
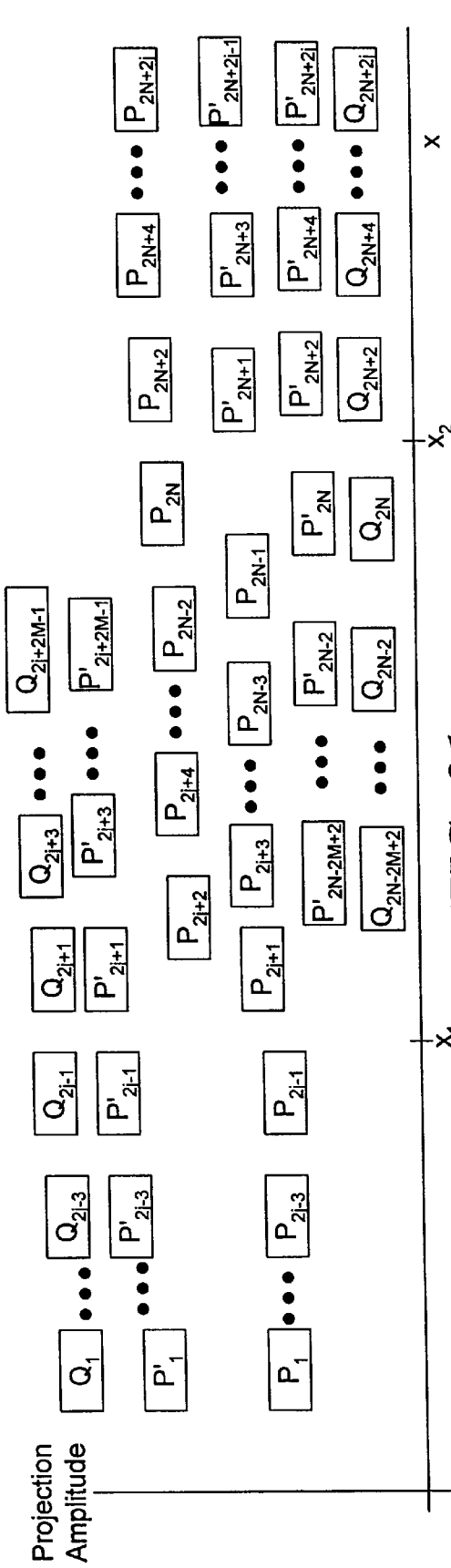
FIG. 21 illustrates a method according to one aspect of the invention for adjusting the extracted data pints to be equivalent to the missing portion of the parallel beam projection of interest.
Figure 22:
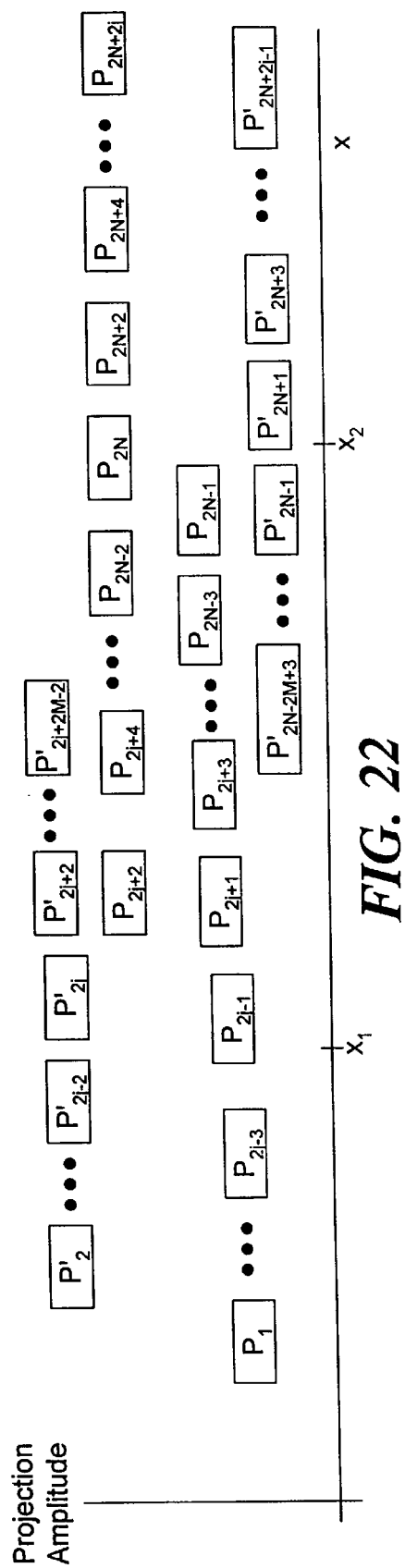
FIG. 22 shows the twice interpolated data points to be interleaved with the parallel beam projection of interest in the exterior regions and to be weighted with the original data points in the boundary regions.

FIG. 21 illustrates the results of the first operation performed by adjuster 520. In this operation, adjuster 520 generates a set of interpolated odd data points $P'_1$ through $P'_{2j+2M-1}$, and a set of even data points $P'_{2N-2M+2}$ through $P'_{2N+2j}$. Based on the results of the first operation, adjuster 520 performs a second operation to generate a set of interpolated even data points $P'_2$ through $P'_{2j+2M-2}$ and a set of odd data points $P'_{2N-2M+3}$ through $P'_{2N+2j-1}$ as shown in FIG. 22. Adjuster 520 attempts to generate the interpolated even data pints $P'_2$ through $P'_{2j+2M-2}$ so that they are estimates of the data points that would have been generated by the missing detector portion 14c for the reordered projection 212, if such detectors had been present in the detector system. Similarly, adjuster 520 attempts to generate the interpolated odd data points $P'_{2N-2M+3}$ through $P'_{2N+2j-1}$ so that they are estimates of the data points that would have been generated by the detectors in the missing portion 14c for the reordered projection 210 if such detectors had been present in the detector system.

More specifically, in the first operation adjuster 520 generates the interpolated odd data points $P'_{2k-1}$ according to a weighted average of the data points of $Q_{2k-1}$ and $P_{2k-1}$ for all integers k from one to j+M. The coefficients for this weighted average are preferably selected so that the Z-axis coordinate of the interpolated odd data points $P'_{2k-1}$ is equal to the z-axis coordinate of the corresponding data point that would have been generated by missing portion 14c for reordered projection 212. Similarly, adjuster 520 generates the interpolated even data points $P'_{2k}$ according to a weighted average of the data pints $Q_{2k}$ and $P_{2k}$ for all integers k from N−M+1 to N+j. The coefficients for this interpolation are selected so that the Z-axis coordinate of the data points $P'_{2k}$ is equal to the Z-axis coordinate of the corresponding data point that would have been generated by the missing portion 14c for reordered projection 210.

In one preferred embodiment, adjuster 520 generates the interpolated odd data points $P_{2k-1}'$ and the even data points $P'_{2k}$ according to the following Equation (10) in the first operation.

$$P'_{2k-1}=c_1 * Q_{2k-1}+c_2 * P_{2k-1}, \text{ for } k=1, 2, \ldots, j+M \quad (10)$$

$$P'_{2k}=c_1 * Q_{2k}+c_2 * P_{2k}, \text{ for } k=N-M+1, N-M+2, \ldots, N+j$$

where $c_1$=0.5−2m/MAX, and $c_2$=1.0−$c_1$

In one preferred embodiment, adjuster 520 interpolates even data points from odd data points $P'_{2k-1}$ and odd data points from even data points $P'_{2k}$ according to the following Equation (11) in the second operation.

$$P'_{2k}=0.5 * (P'_{2k-1}+P'_{2k+1}), \text{ for } k=1, 2, 3, \ldots, j+M-1 \quad (11)$$

$$P'_{2k-1}=0.5 * (P'_{2k-2}+P'_{2k}), \text{ for } k=N-M+2, N-M+3, \ldots, N+j$$

The first two operations performed by adjuster 520 tends to reduce the discontinuities across the symmetry boundary by interleaving the twice interpolated even data points $P'_2$ through $P'_{2j}$ with the original odd data points $P_1$ through $P_{2j+1}$ in one exterior region, and interleaving the twice interpolated odd data points $P'_{2N+1}$ through $P'_{2N+2j-1}$ with the original even data points $P_{2N}$ through $P_{2N+2j}$ in the other exterior region. However, an amplitude offset, or discontinuity often remains between the original data points and the interpolated data points in the exterior regions. This offset remains because the interpolation performed in the first two operations merely estimates the values that actual detectors would have measured and there is an associated error in these estimates. Adjuster 520 therefore preferably performs a third operation during which the adjuster 520 attempts to smooth out the discontinuity caused by this error.

In the third operation, adjuster 520 averages the twice interpolated even data points $P'_{2j+2}$ through $P'_{2j+2M-2}$ with the original even data points $P_{2j+2}$ through $P_{2j+2M-2}$ near the symmetry boundary with a gradual varying weight. Similarly, adjuster 520 averages the twice interpolated odd data points $P'_{2N-2M+3}$ through $P'_{2N-1}$ with the original odd data points $P_{2N-2M+3}$ through $P_{2N-1}$ near the other symmetry boundary with a gradual varying weight. In one preferred embodiment, adjuster 520 performs such averaging according to the following Equation (12) for the even data points $$P''_{2j+2k}=w_1(k) * P_{2j+2k}+w_2(k) * P'_{2j+2k}, \text{ for } k=1, 2, \ldots, M-1 \quad (12)$$

where $w_1(k)$=k/M, and $w_2(k)$=1.0−$w_1(k)$ and the following Equation (13) for the odd data points $$P''_{2N-2k+1}=w_1(k)*P_{2N-2k+1}+w_2(k)*P'_{2N-2k+1}, \text{ for } k=1, 2, \ldots, M(13)$$

where $w_1(k)$=k/M, and $w_2(k)$=1.0−$w_1(k)$

Figure 23:
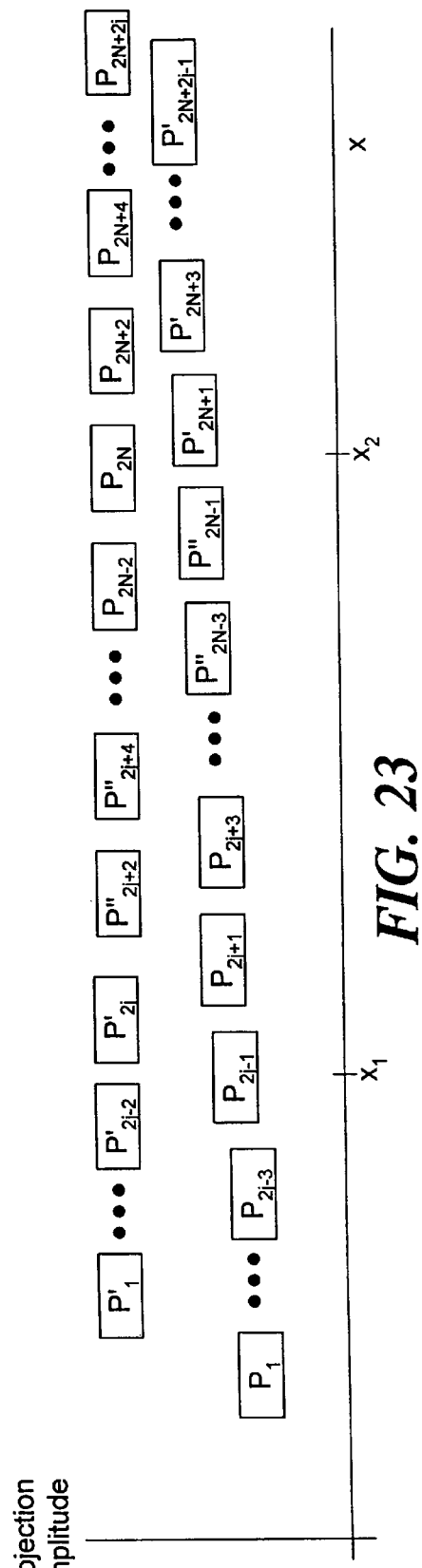
FIG. 23 shows the final adjusted projection with fully interleaved parallel beam projection, in which M−1 points of weighted averages are used in each boundary region to smooth out the discontinuities across the symmetry boundaries.

Adjuster 520 replaces the original even data points $P_{2j+2}$ through $P_{2j+2M-2}$ with weighted averages $P''_{2j+2}$ through $P''_{2j+2M-2}$, and the original odd data points $P_{2N-2M+3}$ through $P_{2N-1}$ by weighted averages $P''_{2N-2M+3}$ through $P''_{2N-1}$ as shown in FIG. 23. The weighted averaging data are also shown in the parallel beam projection 536 of FIG. 19 in two boundary regions 536d and 536e, in which only two average points are shown for simplicity. There are M−1 weighted averages in each boundary region, and the typical number of M is about 16. These weighted averaging data smooth out the discontinuities between the central region and the exterior regions.

Adjuster 520 then uses these smoothed data points to form the adjusted projections and applies these adjusted projections to interpolation system 318. Interpolation system 318, motion filter 410, and back projector 320 then treat the adjusted projections as if they were interleaved parallel beam projections generated from data collected by a symmetric offset detector system.

In tomograms generated by scanners constructed according to the invention (e.g., scanners 300, 400, and 500) the artifacts caused by the Z-axis motion of the patient are reduced to a negligible level. Further, these tomograms provide the high resolution expected from scanners using offset detector systems. The quality of these tomograms is similar to that of tomograms generated from CZA scanning.

In alternative embodiments of the invention, the interpolated projections generated by interpolations systems 318 or 518 may be reordered to fan beam projections and back projector 320 may generate tomograms from this fan beam data by using fan beam reconstruction algorithms.

Since certain changes may be made in the above apparatus without departing from the scope of the invention herein involved, it is intended that all matter contained in the above description or shown in the accompanying drawing shall be interpreted in an illustrative and not a limiting sense.

What is claimed is:

1. A CT scanner comprising:

support means for supporting a radiation source and a detection system in a predetermined spatial relationship and for rotation about a rotation axis, said detection system comprising a plurality of detectors which are offset relative to a center line passing from the radiation source through the rotation axis;

means for providing relative translation between an object being scanned and the support means in the direction of said rotation axis as the radiation source and detection system rotate about said rotation axis so as to provide a helical scan through a predetermined volume of said object;

means, coupled to said detection system, for generating parallel projection data, normal to and at predetermined successive locations along and successive projection angles relative to said rotation axis, as a function of data acquired during said helical scan so that for each projection angle for at least a predetermined number of projection angles, a first set of said parallel projection data is displaced along said rotation axis, antiparallel to and offset from a second set of said parallel projection data;

means, using said second set of parallel data, for generating for each projection angle for said at least a predetermined number of projection angles, a third set of parallel projection data displaced along said rotation axis, antiparallel to and coincident with said first set of parallel projection data; and means, using at least said third set of data and said first set of data, for generating for each projection angle for said at least a predetermined number of projection angles, parallel projection data in a predetermined slice plane.

2. A CT scanner according to claim 1, further including means, using said first set of parallel data, for generating for each projection angle for said at least a predetermined number of projection angles, at least a fourth set of parallel projection data displaced along said rotation axis, antiparallel to and coincident with said second set of parallel projection data; and means, using said fourth set of data and said second set of data to generate for each projection angle for said at least a predetermined number of projection angles, parallel projection data in said slice plane.

3. A CT scanner according to claim 2, wherein said means for generating parallel projection data in a predetermined slice plane includes means for weighting each of the data of said first and third sets of data and each of the data of said second and fourth sets of data, each as a function of the respective axial location of said each of the data relative to the slice plane.

4. A CT scanner according to claim 3, wherein said means for generating parallel projection data in a predetermined slice plane separates said data into at least two terms, with at least one of the terms being multiplied by at least two different scaling factors.

5. A CT scanner according to claim 4, wherein one scaling factor is a function of both the parallel beam projection angle and the detector number, and the other scaling factor is a function of only the detector number.

6. A CT scanner according to claim 4, wherein said scaling factors are stored as lookup tables.

7. A CT scanner according to claim 4, wherein one scaling factor is a function of the equivalent shift in detector and detector number, and the other scaling factor is a function of only the detector number.

8. A CT scanner according to claim 2, wherein said means for generating at least a third set of parallel projection data includes means for interpolating said third set of parallel projection data from said second set of parallel projection data and said means for generating said fourth set of parallel projection data includes means for interpolating said fourth set of parallel projection data from said first set of parallel projection data.

9. A CT scanner according to claim 1, wherein said means for generating at least a third set of parallel projection data includes means for interpolating said third set of parallel projection data from said second set of parallel projection data.

10. A CT scanner according to claim 9, wherein said means for interpolating said third set of parallel projection data includes means for generating said third set of parallel projection data as a function of a Fourier transform process.

11. A CT scanner according to claim 10, wherein said Fourier transform process includes generating a forward Fourier transform of data, generating a second Fourier transform, and generating an inverse Fourier transform.

12. A CT scanner according to claim 11, wherein said second Fourier transform is equal to said forward Fourier transform, except that the frequency range of said second Fourier transform is twice that of said forward Fourier transform.

13. A CT scanner according to claim 9, wherein said means for interpolating said third set of parallel projection data includes means for generating said third set of parallel projection data in accordance with spatial domain processing function.

14. A CT scanner according to claim 13, wherein said spatial domain processing function is a Lagrange interpolation function.

15. A CT scanner according to claim 14, wherein said spatial domain processing function is a fourth order Lagrange interpolation function.

16. A CT scanner according to claim 1, wherein said means for generating parallel projection data in a predetermined slice plane includes means for weighting each of the data of said first and third sets of data as a function of the respective axial location of said each of the data relative to the slice plane.

17. A CT scanner according to claim 16, wherein said means for generating parallel projection data in a predetermined slice plane separates said data into at least two terms, with at least one of the terms being multiplied by at least two different scaling factors.

18. A CT scanner according to claim 17, wherein one scaling factor is a function of both the parallel beam projection angle and the detector number, and the other scaling factor is a function of only the detector number.

19. A CT scanner according to claim 17, wherein said scaling factors are stored as lookup tables.

20. A CT scanner according to claim 17, wherein one scaling factor is a function of the equivalent shift in detector and detector number, and the other scaling factor is a function of only the detector number.

21. A CT scanner according to claim 1, wherein said plurality of detectors are asymmetrically positioned relative to said center line.

22. A CT scanner according to claim 21, wherein
said plurality of detectors are asymmetrically positioned relative to said center line so that the asymmetric portion of said plurality of detectors subtends an angle $\gamma_m$ relative to said source, and said means, coupled to said detection system, for generating parallel projection data, includes
(A) means for acquiring projection data for each of said detectors during said helical scan at a plurality of projection angles through a rotational angle from $-2\gamma_m$ to $2\pi x+2\gamma_m$, wherein x is an whole integer; and
(B) means for generating parallel projection data at a predetermined slice plane using said projection data acquired by each of said detectors during said helical scan for each of said predetermined number of projection angles.

23. A CT scanner according to claim 21, further including a symmetry boundary adjuster for generating adjusted parallel projection data prior to generating said parallel projection data in said predetermined slice plane, and wherein said means for generating parallel projection data in a predetermined slice plane includes means for using said adjusted parallel projection data when generating said parallel projection data in a predetermined slice plane.

24. A CT scanner according to claim 21, wherein said parallel projection data generated normal to and at predetermined successive locations along said rotation axis, as a function of data acquired during said helical scan, includes exterior portions of non-interleaved parallel projection data from either said one set of said parallel projection data or said second set of said parallel projection data, said scanner further including a symmetry boundary adjuster for generating interleaved parallel projection data offset and antiparallel to said non-interleaved parallel projection data so as to provide a complete set of said first and second sets of said parallel projection data so that all of said projection data is interleaved.

25. A CT scanner according to claim 1, further including a motion artifact filter for compensating for non-axial movement induced artifacts in said acquired data.

26. A CT scanner according to claim 25, wherein said motion artifact filter includes a high pass filter for filtering said parallel projection data with respect to said predetermined slice plane so as to provide high frequency data, a low pass filter for filtering said high frequency data so as to provide low frequency data, a threshold converter for providing only low frequency data exceeding a predetermined threshold so as to provide select low frequency data, a weight generator and a multiplier for selectively weighting each of said select low frequency data so as to provide an error, and a substractor for substracting said error from said parallel projection data.

27. A CT scanner according to claim 1, wherein said detectors are asymmetrically arranged relative to said center line.

28. A CT scanner according to claim 1, wherein said means, coupled to said detection system, for generating parallel projection data normal to and at predetermined successive locations along said rotation axis includes means for acquiring fan beam projection data during said helical scan, and means for reordering said fan beam projection data into said first and second sets of said parallel projection data.

29. A CT scanner comprising:

support means for supporting a radiation source and a detection system in a predetermined spatial relationship and for rotation about a rotation axis, said detection system comprising a detector array including a plurality of detectors arranged asymmetrically relative to a center line passing from the radiation source through the rotation axis so that the asymmetric portion of said array subtends an angle $\gamma_m$ relative to said radiation source;

means for providing relative translation between an object being scanned and the support means in the direction of said rotation axis as the radiation source and detection system rotate about said rotation axis so as to provide a helical scan through a predetermined volume of said object; and means, coupled to said detection system, for generating parallel projection data at a predetermined slice plane as a function of acquired projection data acquired by said detectors during said helical scan at a plurality of projection angles through a rotational angle of $2\pi x + 4\gamma_m$, wherein x is a whole integer.

30. A CT scanner according to claim 29, wherein the slice plane is located at $\pi x$.

31. A CT scanner according to claim 30, wherein the parallel projection data acquired between $2\gamma_m$ radians and $2\pi x + 2\gamma_m$ radians is interleaved data.

32. A CT scanner according to claim 29, wherein parallel projection data directly acquired by said detectors includes interleaved and non-interleaved parallel projection data, and said means for generating parallel projection data at said predetermined slice plane includes means for generating additional parallel projection data as a function of said acquired projection data so as to create parallel projection data interleaved with said non-interleaved parallel data.

33. A CT scanner according to claim 32, wherein the means for generating additional parallel projection data includes means for generating said additional parallel projection data as if said data were acquired by detectors positioned so as to make said asymmetric detectors symmetrical about said center line.

34. A CT scanner according to claim 32, wherein said means for generating additional parallel projection data includes means for interpolating additional parallel projection data as if said data were acquired by detectors positioned so as to make said asymmetric detectors symmetrical about said center line.

35. A CT scanner according to claim 32, wherein said non-interleaved data is acquired between 0° and $2\gamma_m$ radians and between $2\pi x + 2\gamma_m$ and $2\pi x + 4\gamma_m$ radians.

36. A CT scanner according to claim 32, further including a symmetry boundary adjuster for generating adjusted parallel projection data at the boundary of interleaved data and non-interleaved data.

* * * * *